United States Patent [19]

Cho

[11] Patent Number: 4,849,227

[45] Date of Patent: Jul. 18, 1989

[54] PHARMACEUTICAL COMPOSITIONS

[75] Inventor: Young W. Cho, Chester, N.J.

[73] Assignee: Eurasiam Laboratories, Inc., Chester, N.J.

[21] Appl. No.: 21,625

[22] Filed: Mar. 3, 1987

Related U.S. Application Data

[63] Continuation-in-part of Ser. No. 842,625, Mar. 21, 1986, abandoned.

[51] Int. Cl.⁴ .......................... A61K 9/16; A61K 9/50
[52] U.S. Cl. ..................................... 424/498; 424/456; 424/460; 424/46.1; 424/463; 424/476; 424/490; 424/499
[58] Field of Search ............... 424/476, 456, 490, 498, 424/499, 460, 461, 463; 514/3

[56] References Cited

U.S. PATENT DOCUMENTS

| | | | |
|---|---|---|---|
| 2,474,729 | 6/1949 | Durel et al. ........................ | 167/7 S |
| 2,574,889 | 11/1951 | Rosenberg et al. ................. | 167/7 S |
| 3,656,997 | 4/1972 | Cordes .............................. | 424/463 |
| 3,922,339 | 11/1975 | Shear ................................ | 424/22 |
| 3,965,260 | 6/1976 | McArthur et al. ................. | 424/177 |
| 3,991,180 | 11/1976 | Boettner et al. .................... | 424/94 |
| 4,173,629 | 11/1979 | Dempski et al. .................... | 424/499 |
| 4,250,163 | 2/1981 | Nagai et al. ....................... | 424/14 |
| 4,356,167 | 10/1982 | Kelly ................................. | 514/3 |
| 4,447,412 | 5/1984 | Bilton ............................... | 424/16 |
| 4,448,765 | 5/1984 | Ash et al. ........................... | 424/14 |
| 4,452,775 | 6/1984 | Kent .................................. | 514/3 |
| 4,454,317 | 8/1984 | Thies et al. ........................ | 264/4.3 |
| 4,529,589 | 7/1985 | Davydov et al. ................... | 514/3 |
| 4,579,730 | 4/1986 | Kidron et al. ..................... | 424/465 |

FOREIGN PATENT DOCUMENTS

| | | |
|---|---|---|
| 0071433 | 2/1983 | European Pat. Off. . |
| 0127535 | 5/1984 | European Pat. Off. . |
| 0142085 | 5/1985 | European Pat. Off. . |
| 0140085 | 8/1985 | European Pat. Off. . |
| 0130779 | 9/1985 | European Pat. Off. . |
| 0143949 | 12/1985 | European Pat. Off. . |
| 285091 | 6/1929 | United Kingdom ................ 424/476 |
| 461317 | 2/1937 | United Kingdom ................ 424/476 |
| 2013087 | 8/1979 | United Kingdom . |
| 2050287 | 8/1979 | United Kingdom . |

OTHER PUBLICATIONS

G. Maierhofer, Liposomes: Preparation and Application, American Laboratory, Oct., 1985.

Poznansky and Juliano, Biological Approach to the Controlled Delivery of Drugs: A Critical Review, Pharmacologist Reviews, 1984.

Primary Examiner—Frederick E. Waddell

[57] ABSTRACT

A composition adapted to administer a pharmocologically effective amount of a pharmaceutical agent when ingested orally comprising (a) a pharmaceutical agent; (b) a lipid coating materials; and (c) an enteric coating materials optionally comprising water soluble coating materials; emulsifying and solubilizing agents; binding agents; stabilizing and enzyme inhibiting agents surfactants and antimicrobial agents. The composition can also include a low density lipoprotein composition and lipolytic enzymes.

69 Claims, 16 Drawing Sheets

FIG. 4
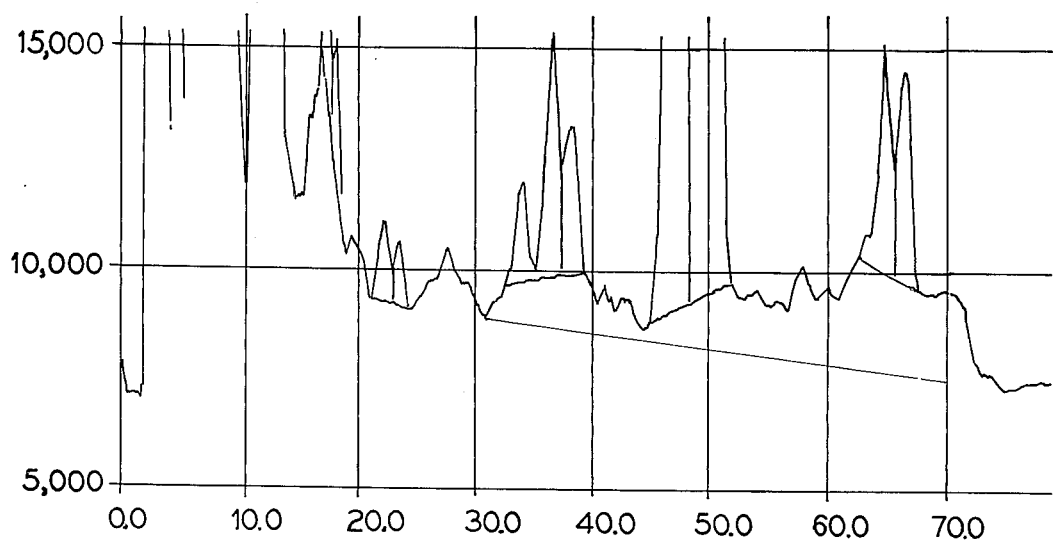
FIG. 5
FIG. 6

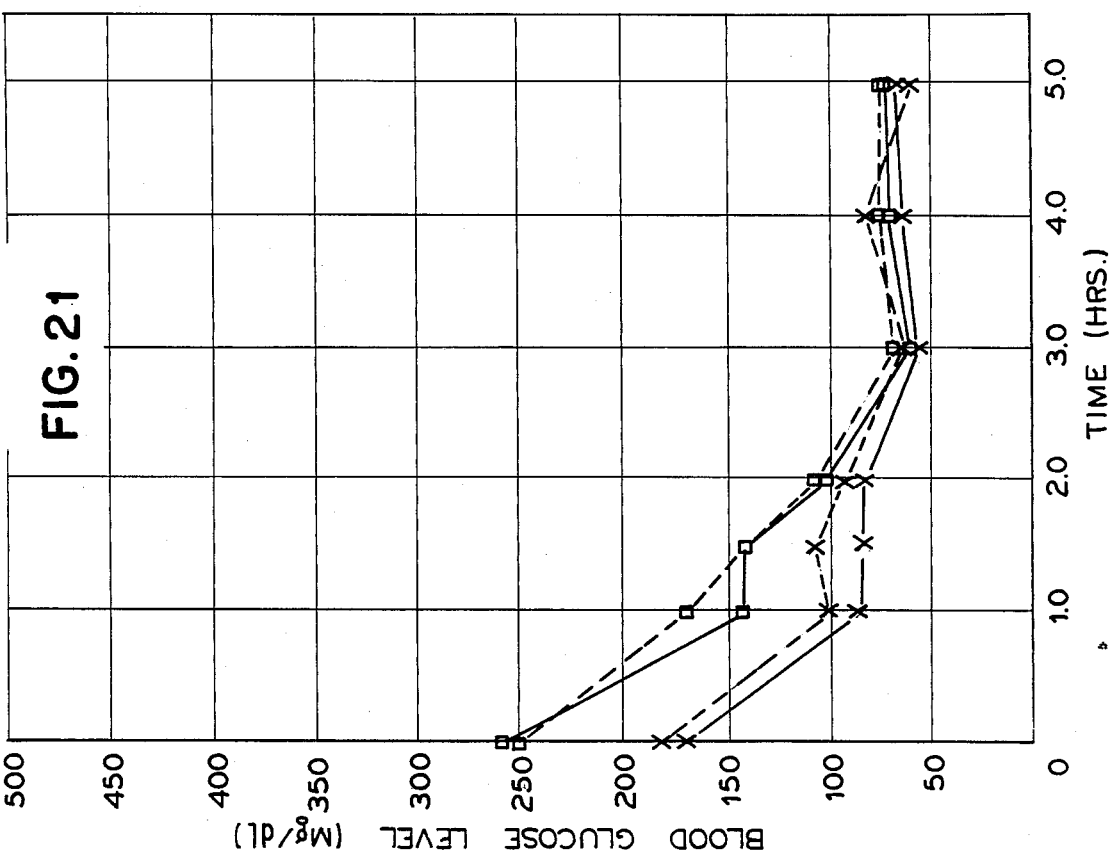
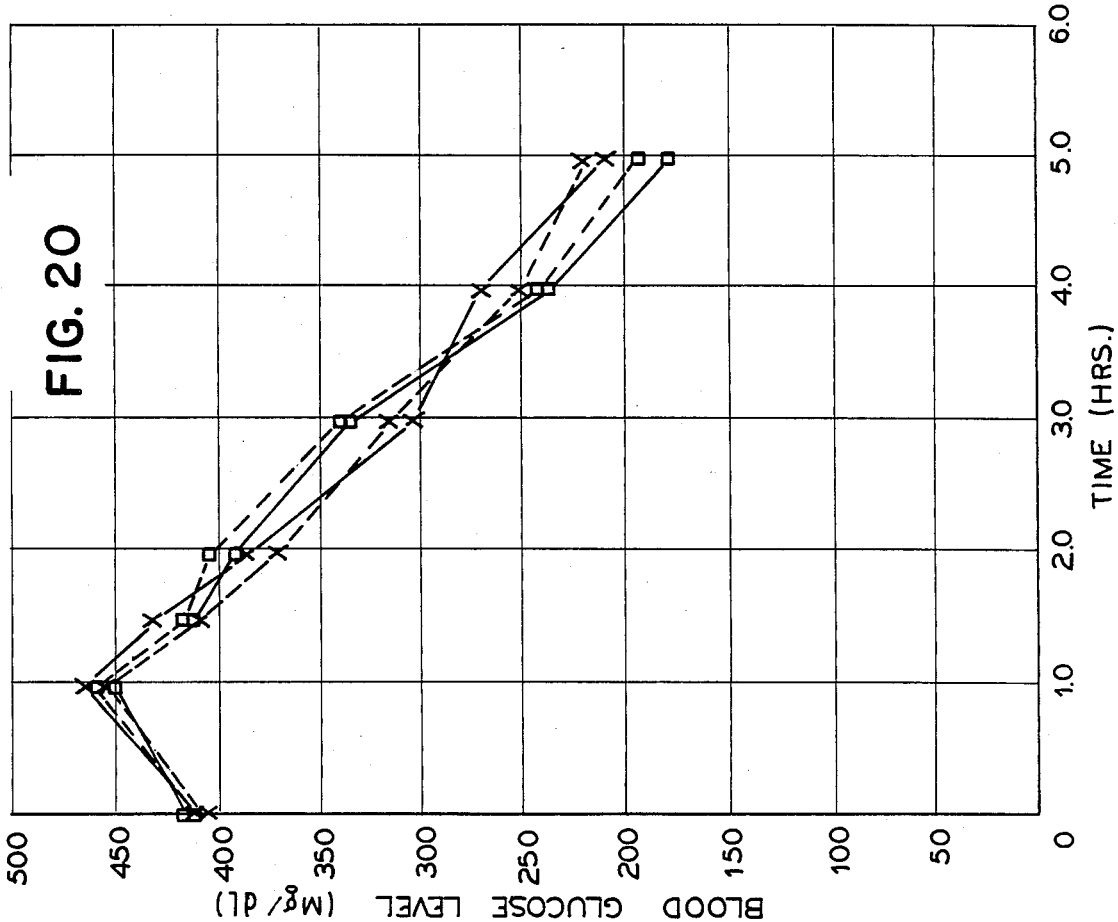

PHARMACEUTICAL COMPOSITIONS

This application is a continuation-in-part of Ser. No. 06/842,625 filed Mar. 21, 1986, now abandoned.

BACKGROUND OF THE INVENTION

The present invention relates generally to compositions for the oral administration of proteinaceous materials in biologically active form and methods and apparatus of making same. More particularly, the present invention relates to compositions for the treatment of diabetes by oral administration of insulin.

Many drugs, medicaments, and therapies are administered parenterally because they are degraded or not adequately absorbed in the stomach and gastrointestinal tract and therefore cannot be administered orally. For example, as discussed in detail below, insulin is administered through subcutaneous shots to many patients suffering from diabetes mellitus.

Diabetes mellitus is a chronic disorder affecting carbohydrate fat and protein metabolism. It is characterized by hyperglycemia and glycosurea resulting from a defective or deficient insulin secretory response. Two major variants of the disease exist. The number of patients diagnosed as diabetic is estimated to be 10 million in the United States alone and this figure is believed to be increasing at a rate of 6% per year.

One variant, seen in about ten percent of all idiopathic diabetics, is referred to as insulin-dependent diabetes mellitus ("IDDM") or juvenile onset diabetes. This variant is frequently manifested for the first time in youth and is characterized by a progressive loss of insulin secretory function by beta cells of the pancreas and hence a pregressive "dependency" on exogenous insulin for maintenance of carbohydrate metabolism. (This characteristic is shared by those non-idiopathic, or "secondary", diabetics whose disorders have their origins in pancreatic disease.) The second variant of idiopathic diabetes mellitus is referred to as non-insulin-dependent diabetes mellitus ("NIDDM") or adult onset diabetes mellitus and accounts for the remainder of the idiopathic diabetic population.

All diabetics, regardless of their genetic and environmental backgrounds or the age of onset of the disease, have in common an apparent lack of insulin or inadequate insulin function. Because transfer of glucose from the blood to the muscle and fatty is insulin dependent, diabetics lack the ability to utilize glucose adequately. Further, because glycogenolysis is ordinarily inhibited by insulin, the rate of glycogenolysis is elevated in the diabetic. Both these "derangements" from normal metabolic events lead to accumulation of glucose in the blood (hyperglycemia) to the point where renal glucose reabsorption capacity is exceeded and glycosuria occurs. The major source of energy for the diabetic thus becomes fatty acids derived from triglycerides stored in fatty tissue.

In the liver, fatty acids are oxidized to ketone bodies which are circulated and used as an energy source by tissues. In the IDDM patient, and sometimes the NIDDM patient, the rate of formation of the ketone bodies may exceed their rate of their utilization and ketosis along with metabolic acidosis may occur. Since tissues appear to be starving for glucose, dietary and tissue sources of protein are used in glucogenesis. Anabolic processes such as synthesis of glycogen, triglycerides and proteins are "sacrificed" to catabolic activities including glycogenolysis, gluconeogenesis and mobilization of fats. Thus, the diabetic state which has its origins as a "simple" insulin defect, results in widespread metabolic disturbances having long-term pathological effects on nearly all organs and tissues of the body. Indeed, the diabetic state is one of the prime contributors to deaths caused by myocardial infarction, renal failure, cerebrovascular disease, atherosclerotic heart disease, and systemic infections.

The hyperglycemic and glycosuric conditions of the diabetic disease may be remedied by a manipulation of the diet, control of body weight, and regulation of physical activity. In some diabetics, particularly those suffering from NIDDM, the hyperglycemic and glycosuric conditions can be managed by oral administration of anti-hyperglycemic agents such as derivatives of sulfonylureas, sulfonamides, biguanides and other compounds. For diabetics suffering from IDDM and advanced NIDDM, however, therapy has focused on administration of exogenous insulin.

Insulin is a polypeptide produced in the islets of Langerhans located in the pancreas. The insulin molecule is initially sythesized as a single polypeptide chain but is processed such that in its active form it consists of two amino acid chains joined by two cysteine disulfide bonds. One of the two chains is folded back upon itself as a result of a third disulfide bond. The entire molecule has a molecular weight of 5,734 and is dependent upon the disulfide bonds to maintain its biologically active conformation.

While in the past, exogenous insulin has been derived primarily from bovine and porcine sources it has recently been obtained in "human" form as a result of recombinant DNA technology. The availability of "human" insulin derived from recombinant sources has proven to be greatly beneficial to those diabetics with an intolerance to insulin derived from animal sources.

Nevertheless, the greatest problem with respect to insulin therapy is not related to the source of the insulin but rather to its method of introduction to the body. The most common method for the administration of insulin is that of subcutaneous injection. This method is inconvenient, painful, and may itself exacerbate the pathology of the disease. Subcutaneous injection of insulin gives rise to relatively high insulin levels in peripheral tissues and relatively low levels circulating through the liver, the primary site of endogenous insulin activity. High levels of insulin in peripheral tissue have been associated with blood vessel pathology (e.g., blood vessel constriction and permeability changes) and pathologic effect on associated peripheral tissues, e.g., diabetic retinopathy. The "swamping" effects of subcutaneously administered insulin on peripheral circulatory tissues eventually reduces the amount of insulin circulating to the liver—again resulting in the need for increased doses to achieve desired metabolic effects. For these various reasons an alternative to injection as a method for the administration of insulin has long been sought.

As an alternative to the injection of insulin, some workers have directed their effort toward the intra-rectal administration of insulin by means of suppository. U.S. Pat. No. 2,373,625 issued to Brahn, discloses insulin suppositories containing weak organic acids such as lactic acid or citric acid in combination with a surfactant.

Also known in the art are insulin suppositories utilizing a variety of ingredients such as saponin, corn oil, polyoxyethylene-9-lauryl-alcohol and polyoxyethylenelaurylether. Insulin has also been encapsulated into acrylic acid-base water soluble gels and into soft gel capsules containing surfactants. Although the method of intra-rectal administration of insulin shows promise the results of bioavailability tests have been inconsistent and the method is inconvenient.

Ishida, et al., Chem. Pharm. Bull., 29, 810 discloses a method whereby insulin may be administered via the buccal mucosa of the mouth. Insulin was mixed with a cocoa fat base and a surfactant before administration to the buccal mucosa. Experiments in dogs demonstrates only poor bioavailability of insulin so administered.

Other workers have directed their efforts towards intrapulmonic administration of insulin. Wigley, et al., Diabetes, 20, 552 (1971) discloses administration by means of a nebulizer of insulin at 500 U/ml in particles 2 m in diameter. A hypoglycemic response was observed after 30 U/kg of body weight which indicated a total bioavailability of roughly 7 to 16%. Yoshida, et al., J. Pharm. Sci. 68, 670 (1979) discloses an intra-pulmonic introduction of insulin combined with lactose and acethylglycerinemonstearate, dissolved in fluoroethane. The aerosol induced hypoglycemic response when administered at an amount 2.5 U/Kg of body weight to rabbits.

Another method of administering insulin that has demonstrated promise is the intra-nasal administration of insulin. Hirai, et al., Int. J. Pharm., 9, 165 (1981) discloses the intra-nasal administration of insulin in combination with a surfactant such as sodium glycocholate solution. Nagai, et al., Journal of Controlled Release, 1, 15 (1984) discloses high bioavailability of insulin when administered intra-nasally to dogs. In this method, crystalline insulin was dissolved into a 0.1 N HCl solution to which a surfactant was added. The solution was then adjusted to a pH of 7.4 by addition of a 0.01 N NaHCl solution and freeze dried. The solution was then mixed with crystalline cellulose prior to its nasal administration.

In the search for alternative methodologies for the administration of insulin it is the oral administration of insulin that has received the most attention. A methodology for the oral administration of insulin would be highly desirable for reasons of safety, convenience, and comfort and would avoid many of the shortcomings suffered by methods involving injection of insulin. Despite the apparent desirability of methods for oral delivery of insulin two major difficulties have limited the success of attempts to fashion oral insulin therapeutics.

The first major difficulty in fashioning oral insulin therapeutics is that the insulin polypeptide is inactivated in the gastrointestinal tract by enzymes such as trypsin, chymotrypsin and other lytic enzymes. The insulin polypeptide is a relatively simple one and with its two disulfide bonds is easily degraded under the harsh conditions of the stomach and gastrointestinal tract.

The second difficulty with the oral administration of insulin is that even if the polypeptide evades degradation in the stomach and gastrointestinal tract it is poorly, and inconsistently, absorbed through the gastrointestinal membrane. Because of its poor bioavailability large oral doses must be given to ensure a hypoglycemic effect. Because inconsistent amounts of insulin are made available, the advantages of an oral administration method may be outweighed by the fact that under-or overdoses of insulin can be more of a health hazard than no insulin at all.

Several approaches have been followed in attempting to overcome the inherent difficulties of oral insulin administration. Some of these approaches include attempts to either inactivate the lytic gastrointestinal enzymes responsible for inactivation of the insulin function or to provide insulin analogues resistant to inactivation by such enzymes. Sichiri, et al., To-Nyo-Byo (Japanese Diabetes Publication), 18:619, 1975, discloses an insulin analogue (beta-Naphthyl-azo-Polystearryle-insulin) which when administered orally to rabbits at 150 IU/Kg body weight induced a hypoglycemic response. Other workers have attempted to make alkyl compounds of insulin by adding triethylamine HCl as well as a surfactant. Teng, oral presentation at the American Diabetic Society Meeting, May, 1983, San Antonio, Tex.

Attempts to prevent insulin degradation by inactivation of lytic enzymes in the gastrointestinal tract have met with some success. Danforth, et al., Endocrinology, 65, 118 (1959) discloses an insulin composition administered orally with isopropylfruorophosphate (an inhibitor of trypsin and chymotrypsin) and indole-3-acetate (an inhibitor of the enzymes known as "insulinase" found in the liver). The composition was found to induce a hypoglycemic effect when administered orally to rats. Other workers have disclosed mild (equivalent to 3% bioavailability of insulin) hypoglycemic responses after the oral administration of insulin along with pancreas inactivating agents (Laskowski, et al., Science, 127, 1115 (1958)). Other workers have found that the oral administration of insulin results in low bioactivities as a result of insulin inactivation in the stomach by pepsin and because of poor absorption through the intestinal membrane (Crane, et al., Diabetes, 17, 625 (1968)).

Workers have also attempted to increase the bioavailability of orally administered insulin by administering the insulin with surfactant agents. The use of surfactant agents such as polyethylene glycol-1000 monoacetyl ether and sodium lauryl sulfate with triethylamine HCl have demonstrated the ability to increase insulin bioavailability to some degree; although 35 units of insulin administered orally had an effect on the blood sugar level equivalent to that of only 4 units administered intravenously (Touitou, et al., J. Pharm. Pharmacol., 32, 108 (1980)).

Efforts have also been directed toward the oral administration of insulin in conjunction with an emulsion system. One group of investigators (Sichiri, et al., Acta Diabet. Lat., 15, 175 (1978)) disclose that they observed a hypoglycemic effect upon administering a water/oil/-water emulsion system with added insulin to rats. A 250 IU/Kg of body weight dose was reported to produce an effect equivalent to a 10 IU/Kg dose administered intramuscularly. Insulin has also been administered by means of other emulsion systems utilizing fat soluble vitamins although the hypoglycemic effects in animals such as dogs have been mild and not dose responsive.

Some of the most promising efforts towards increasing the bioavailability of orally administered insulin lie in efforts to microencapsulate insulin materials. Insulin has been microencapsulated in acrylic acid esters (Sichiri, et al., Acta. Diabet. Lat., 15, 175 (1978)) and the use of high molecular polymers has also been disclosed. Other workers have microencapsulated insulin in liposomes of various lipid compositions. Insulin containing liposomes have been formed with compositions such as phosphotidyl choline, cholesterol and stearylamine;

dimyristoyl phosphatidylcholine; dimyristoyl phosphatidylcholine and cholesterol as well as with lecithin and cholesterol and other materials.

Dobre, et al., Rev. Roumanian Med.-Encdocrinol 22, 253 (1984) discloses methods of entrapping insulin into liposomes for oral administration. Various materials for the construction of liposomes are disclosed including: egg yolk phosphatidyl choline, cholesterol, stearylamine, and dipalmitoylphosphatidyl choline. Even liposome coatings, however, fail to completely protect the enclosed insulin from the degradation effects of hydrochloric acid found in the stomach and enzymes such as pepsin, trypsin and chymotrypsin found in the gastrointestinal tract.

Yoshida, et al., EPA 140,085 discloses insulin containing lipid vesicle preparations comprising lipid vesicles which are composed of an inner aqueous phase in the form of an aqueous solution or suspension of phospholipid.

SUMMARY OF THE INVENTION

The present invention provides compositions that are adapted to administer pharmacologically effective amounts of proteinaceous compounds when ingested orally. It has surprisingly been found that pharmaceutical agents susceptible to degradation within the gastrointestinal tract and lacking the ability to be successfully absorbed into the body through the same can be coated in such a way as to provide for their absorption into the body in pharmacologically effective amounts.

The improved compositions comprise: (a) a pharmaceutical agent; and (b) lipid coating materials; and may include (c) enteric coating materials. The pharmaceutical agent is coated by an inner coating comprising the lipid coating materials and by an outer coating comprising the enteric coating materials. The composition may include, or can be administered with, lipolytic enzymes. The compositions may additionally comprise water soluble coating materials, binder materials, surfactant materials, emulsifiers, stabilizers, antimicrobial agents, and enzyme inhibitors.

In another embodiment of the present invention, the improved compositions comprise: (a) a pharmaceutical agent; (b) lipoprotein materials; and (c) a lipid coating, and may include (d) a water soluble coating and (e) an enteric coating material. The pharmaceutical agent is bound to the lipoprotein and the resultant product may be coated with a water soluble coating and then coated with a lipid inner coating that may be coated with an enteric outer coating. The composition may include, or can be administered with lipolytic enzymes. The compositions may additionally comprise binder materials, surfactant materials, emulsifiers, stabilizers, antimicrobial agents, and enzyme inhibitors.

In one embodiment of the invention, insulin is mixed with a composition comprising emulsifier/solubilizing agent, surfactant, enzyme inhibitor, anti-foaming agent and antimicrobial agent. The mixture is then coated with a lipid coating comprising polyethylene glycol fatty acid esters. The material is then either further coated with an enteric coating and then placed into either hard gel capsules or tablets or placed into a capsule or tablet that is then coated. Each tablet or capsule weighs 250 mg and contains 16 International Units of porcine crystalline insulin.

In another embodiment of this invention, insulin is mixed with a composition comprising at least one: lipid; amino acid; binder; enzyme inhibitors; anti-foaming agent; and water soluble material. The mixture is then coated with a lipid coating comprising triglycerides, phospholipids and cholesterol. The resultant product is then placed into a gel capsule and enteric coated.

In a further embodiment of the present invention, the oral insulin formula comprises granules having a size of approximately 2.00 mm. Preferably, citric acid particles are coated with sodium bicarbonate to create a particle that is then coated with a lipid. The resultant particle is coated with an oral insulin formulation and then with an enteric solution.

In a still further embodiment, insulin particles that have been coated with a lipid coating layer and then enteric coated are placed into a capsule with enteric coated particles of lipase and bile salt. Preferably sodium bicarbonate and citric acid is also added to the capsule.

The apparatus for making the composition comprises a vessel having a chamber. At the bottom of the chamber a perforated rotating disk, air flow means, and chopper are located. Located above the bottom of the chamber are nozzles. To create the composition, particles are placed in the bottom of the chambers and chopped by the chopper. The air flow means causes the particles to be suspended within the chamber. A pharmaceutical agent is sprayed through the nozzles so that the agent binds with the particles. After the agent binds to the particles the bound particles are then coated with a lipid coating sprayed through the nozzles. After the lipid coating is applied, an enteric coating can be applied.

BRIEF DESCRIPTION OF THE DRAWINGS

FIG. 4 is a chromatograph of the composition of Example 1.

FIG. 5 is a photomicrograph of the composition of Example 1.

FIG. 6 is a photomicrograph of the composition of Example 1.

FIG. 20 is a comparison of injectable insulin versus Example 6.

FIG. 21 is a comparison of injectable insulin versus Example 6.

DETAILED DESCRIPTION OF THE PRESENTLY PREFERRED EMBODIMENTS

Figure 1:
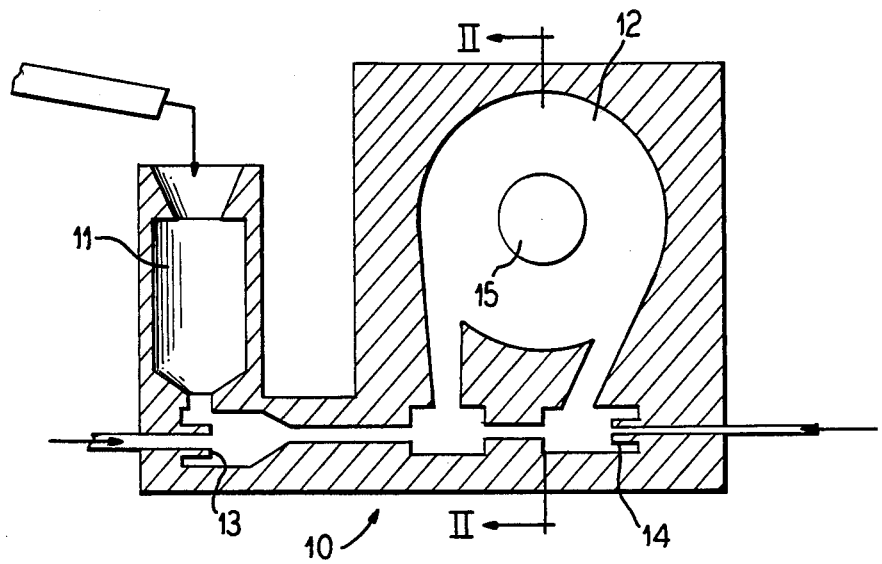
FIG. 1 illustrates a cross-sectional schematic view of a jet mill.

The present invention provides a composition adapted for oral administration of a selected proteinaceous compound material in a biologically active form. As previously discussed, many drugs, medicaments and therapies cannot be orally administered because they degrade or are not well absorbed in the stomach and/or gastrointestinal tract. Example of these drugs include, inter alia: insulin—for treating diabetes; urokinase—for treating thrombosis; Factor VIII—for treating hemophilia; leuprolid—for treating prostrate cancer; gangliocides—for improving neurotransmission; vincrostine—for treating cancer; belomyein—for treating cancer; adriamycin—for treating cancer; lidocane—for treating cardiac arrhythmia; and cephalosporidines—for treating infection. Other drugs and medicaments are poorly absorbed when administered orally, e.g., gentamicin, erythromycin, bretylium tosylate, cetiedile, cyclandelate, and chloramphenicol.

For most patients the oral administration of these drugs would be more convenient and for some more therapeutic. The present invention provides a composition that allows proteinaceous compounds, that previously had to be administered parenterally, to be administered orally in pharmacologically effective amounts.

To this end, in an embodiment of the invention, the composition includes particles consisting essentially of solid emulsifying agents and surfactants, to which a selected biologically active proteinaceous material is bound to the surface of the particles with a binder agent. A lipid coating is then applied over the particles and proteinaceous material. The particles can have an average diameter of approximately 1 micron to about ½ millimeter but preferably, the particles have an average diameter of approximately 1 to about 100 microns. The lipid coating is preferably coated on to the particles and proteinaceous material at a thickness of approximately 0.05 to 1.0 microns. The lipid coating can be coated by an enteric coating layer.

In another embodiment of the invention, the proteinaceous material is bound to lipoprotein particles. The particles can have an average diameter of 1 micron to ½ millimeter but preferably, the particles have an average diameter of 1 to 100 microns. The particles are then coated with a water soluble material and the resultant product is coated with a lipid coating. The lipid coating preferably has a thickness of approximately 0.1 to about 0.3 microns. The resultant product may be placed in a gel capsule and may then be enteric coated to a thickness of approximately 0.1 microns to about 0.3 microns.

In another embodiment, the proteinaceous material is coated over granules. The granules are formed by coating sodium bicarbonate and, if desired, a small amount of starch, over particles of citric acid (preferably 100-150 grams in size). A formulation including the proteinaceous material is then coated over the granule. The resultant product is then enteric coated. The resultant granules preferably have a size of less than 2.0 mm. Physiologically, a granule size of less than 2.0 mm can be rapidly dumped into the duodenum. By encapsulating the granules in small hard gel capsules, as opposed to larger gel capsules, intestinal absorption is also increased. The use of sodium bicarbonate and citric acid, either in making the granules or used with the formulation as a powder, promotes a rapid bursting and opening of the capsules or the granule and thus releases the proteinaceous material in the duodenum. Of course other compounds can be used to promote this bursting effect, such as for example, sodium citrate and other bicarbonates, such as, for example, potassium bicarbonate.

The enteric coating assures that the composition passes into the intestinal tract without being degraded in the stomach. In the intestinal tract the coating dissolves. The lipid coating assures that the composition will pass into the user's lymphatic system. To this end, the lipid coating provides the composition with an affinity toward the villae (the terminal openings of the lymphatic system in the intestinal membrane). If the pharmaceutical agent is bound to lipoprotein particles, these particles increase the agent's absorption into the tissue. Lipoproteins have been found to easily penetrate through the cellular membrane and therefore provide a vehicle for bringing the agent into the user's tissue.

It is believed, at this time, that when the pharmaceutical agent is insulin, lipolytic enzymes should also be administered. The lipolytic enzymes can be combined with the composition, or be given in a separate tablet or capsule. The lipolytic enzymes enhance the absorption of the lipid coated material into the villae.

The preferred ingredients for the composition of the present invention will now be set forth.

PROTEINACEOUS MATERIAL

The biologically active proteinaceous material or pharmaceutical agents useful in the present invention may include, but are not limited to, those agents which are susceptible to degradation within the gastrointestinal tract or which are poorly absorbed into the body from the gastrointestinal tract. These agents including insulin, whether from animal or recombinant source, as well as other pharmaceutical agents including inter alia, urokinase, Factor VIII, leuprolid, gangliocides, vincristin, belomyein, lidocaine, cephalosporidines, gentamicin, bretylium tosylate, cetiedil, cyclandelate, erythromycin, chloramphenicol, adriamycin, and streptokinase.

LIPID COATING MATERIALS

Lipid coating materials useful in the invention include those chyclomicron-like materials which are attracted by and to the villae of the small intestine. Such materials include, but are not limited to, polyethylene glycol fatty acid esters, glycerophosphatides, phosphatidylephosphates, egg yolk lecithin, oleic acid, stearic acid, palmitate, cholesterol, mono, di, and tri-glycerides, cholesterol ester, yolk lecithen containing 5 to 20% phosphatidic acid, linoleic acid, linolenic acid, lauric acid, phosphatidyle phosphate, glycerine, soy bean oil, sesame seed oil, and tromethan. These lipid coating materials after being coated onto the surface of the pharmaceutical agent, not only seal the pharmaceutical agent but also increase the "affinity" and "absorption" of such pharmaceutical agent-particles to and toward the villae, i.e., the terminal openings of the lymphatic vessels at the intestinal membranes so that the agent is absorbed into the lymphatic system.

A lipid coating composition that has been found to function satisfactorily is as follows:
80 to 90% of lipid may be in a form of mono-, di-, and tri-glycerides;
6 to 9% of Phospholipids;
2% of Cholesterol-Ester and 1% of Free Cholesterol; and
Less than 1% of Free Fatty Acids (NEFA)
About 2% of low molecular protein/amino acid may also be added.
The Cholesterol Esters are:
30% as Cholesterol-Linoleic Acid Ester;
20% as Cholesterol-Oleic Acid Ester; and,
22% as Cholesterol-Palmitic Acid Ester.

ENTERIC COATING MATERIALS

Enteric coating materials useful in the present invention include those coating materials resistant to degradation in the stomach but which will decompose in the environment of the intestinal tract to expose the coated material. Such enteric coating amterials include, but are not limited to, the following ingredients either singly or in combination: hydroxypropyl methylcellulose phthalate, polyethylene glycol-6000, and shellac and they may be dissolved in solvents including dichloromethane, ethanol and water, cellulose phthalate, or polyvinyl acetate phthalate.

A preferred enteric coating material for coating insulin comprises 4.5 parts by weight hydroxymethylcellulose to 0.5 parts shellac, to 0.5 parts polyethylene glycol-6000. This material is dissolved in 47.3 parts dichloromethane and 37.8 parts ethanol. The enteric coating material is then diluted with water to an optimal concentration and is applied to the compositions of the invention.

LIPOPROTEIN MATERIALS

The lipoprotein materials useful in the present invention comprise those lipids and proteins that can be combined to form low density lipoproteins. Preferably the low density lipoproteins mimic the low density lipoprotein profile in humans.

The lipid component includes, but is not limited to, cholesterol, oleic acid, stearic acid, sodium lauryl sulfate, lecithins, sodium lauryl sulfate with lecithins, phosphatides, palmitic acid and phosphatide phophate choline.

The protein component includes, but is not limited to, any of the amino acids or low molecular weight protein. The most preferred amino acids include arginine, lysine, histidine and aspartic acid, and the most preferred proteins include albumin and globulin.

Preferably the lipids are combined with the low molecular weight protein or amino acid at a ratio of between 1:1 to about 3:1 by molecular weight. In a preferred embodiment, the lipids and proteins are combined at a ratio of 1:1.

A lipid composition comprising Cholesterol Ester (46%), Free Cholesterol (14%), Phospholipids (25%), Fat (14%), and NEFA (FFA) about 1% has been found to work satisfactorily when combined with 20-25% by weight amino acids.

WATER SOLUBLE COATING MATERIALS

Water soluble coating materials useful in the present invention include those compounds that provide a hydrophillic coating, including, but not limited to, hydroxypropylmethylcellulose phthalate, polyethylene glycol-6000, hydroxypropylmethylcellulose, hydroxypropylcellulose, crystaline cellulose and shellac, dissolved in dichloromethane, ethanol and water, cellulose phthalate, and polyvinyl acetate phthalate. If the proteinaceous materials are bound to the lipoproteins, and are coated with a water soluble coating, preferably they are coated with a coating having a thickness of approximately 0.05 to about 0.5 microns.

BINDER MATERIALS

Binder materials useful in the present invention are those compounds that bind a peptide to a lipid or lipoprotein. These include, but are not limited to, microcrystalline cellulose, methyl cellulose, ethyl cellulose, sodium carbonxymethylcellulose, hydroxypropylcellulose, methylhydroxypropylcellulose gelatin, povidone, and polyethylene glycol fatty acid ester groups.

LIPOLYTIC ENZYMES

Lipolytic enzymes useful in the present invention are those enzymes that promote absorption of lipids into the villae. These enzymes include, inter alia, lipase, including pancreatic lipase, amylase, protease, and bile salts. Intestinal absorption of fatty acids and lipids is enhanced and promoted by pancreatic lipase in the presence of bile salt. Accordingly, when the proteinaceous material when it is coated by a lipoprotein pancreatic lipase in the presence of bile salt will increase the absorption of the proteinaceous material. If needed, the lipolytic enzymes may be combined with the composition or administered as a separated tablet or capsule. A lipolytic enzyme mixture that has been found to work satisfactory when the pharmaceutical agent is insulin includes: pancreatic lipase, amylase, protease, and bile salts.

FILLER

If the proteinaceous material is bound to a lipoprotein, a filler may be used. The filler may or may not be used as a physical binding agent. The filler may include, but is not limited to gum acacia, crystaline cellulose, hydroxypropylcellulose, and hydroxpropylmethylcellulose.

SURFACTANT MATERIALS

Surfactant materials useful in the present invention include those compounds that prompt better absorption into the villae, and include, but are not limited to, cationic, anionic or nonionic surfactants such as sodium lauryl sulfate, stearyl amine, polyglycerine fatty acid esters, polyethylene alkyl ethers polyoxyethylene alkyl phenyl ethers, fatty acid monoglycerides, sorbitan fatty acid esters, polyoxyethylene fatty acid amines, and polyethylene glycol fatty acid esters.

EMULSIFYING AGENTS

Emulsifying agents useful in the present invention include those compounds that create an emulsion in vivo, and include, but are not limited to, the materials, and combinations of materials, such as cholesterol, stearic acid, sodium stearate, palmitic acid, sodium palmitate, oleic acid, sodium oleate glyceryl monostearate, polyethylene 50 stearate, polyoxyl 40 stearate, polysorbate 20, polysorbate 40, polysorbate 60, polysorbate 80, propylene glycol diacetate, and propylene glycol monostearate. The emulsifying agent can also include those chemical materials and constituents that make it similar to "low density lipoproteins" found in human plasma, such as, arginine HCl, gum aecacia, cholesterol, cholesterol ester, phospholipids, and fatty acids.

STABILIZERS AND ENZYME INHIBITORS

Stabilizers and enzyme inhibitors useful in the present invention are those compounds capable of inactivating or inhibiting the action of degradation mammalian enzymes such as peptidases, proteases, phosphorylases, glutathione-insulin-transhydrogenase, and insulin degrading enzyme, i.e., insulinase. The stabilizer compounds include, but are not limited to, stearylamine, stearyl alcohol, citric acid, lactic acid, triethylamine HCl pyrophosphate, triethanolamine, ovomucoid, ethylendiamine tetraacetate, iodoacetamide, phenylhydrazine, hydroxylamine and 8-hydroquinoline.

ANTIMICROBIAL AGENTS

Antimicrobial agents useful in the present invention are those compounds capable of preventing microbial contamination and degradation of the pharmaceutical compound and its associated binders coatings and additives. In choosing an antimicrobial agent, the microbic activity of the agent must be balanced against its compatibility with other components of the pharmaceutical composition as well as its inherent toxicity to the organism treated therewith. Antimicrobial compounds which generally meet these requirements include but are not limited to methylparaben, ethylparaben, propylparaben, butylparaben, phenol, dehydroacetic acid, phenylethyl alcohol, sodium benzoate, sorbic acid, thymol, thimerosal, sodium dehydroacetate, benzyl alcohol, butylparaben, cresol, p-chloro-m-cresol, chlorobutanol, phenylmercuric acetate, phenylmercuric borate, phenylmercuric nitrate and benzalkonium chloride.

The invention will be more fully understood by reference to the following examples.

EXAMPLE 1

In this example a composition adapted for the oral administration of insulin is prepared according the invention. Particles having an average diameter of approximately 50 microns were prepared from a mixture of cholesterol, sodium lauryl sulfate, and methyl and propylparabens (pH6) as antimicrobial preservatives. The particles were prepared by using a Jet Mill available from Freund International Ltd., Tokyo, Japan.

Figure 2:
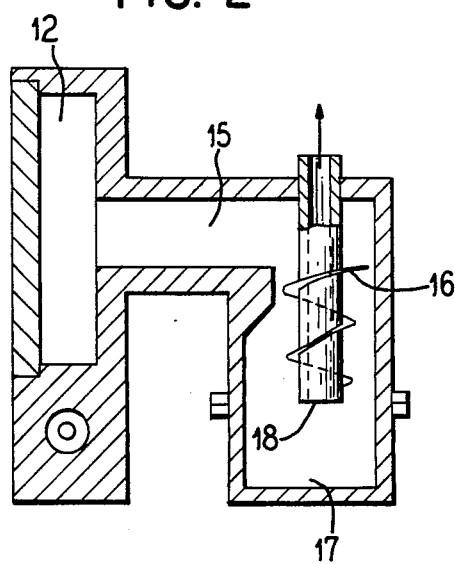
FIG. 2 illustrates a cross-sectional view of the jet mill of FIG. 1.

FIGS. 1 and 2 schematically illustrate the Jet Mill 10. The particles to be prepared are fed into the inlet chamber 11 by a vibrator feeder. The particles in the inlet chamber are carried into a milling chamber 12 by an air flow through an air nozzle 13. A counter air flow is applied through air nozzle 14 opposing the flow of the air carrying the particles in suspension. The air flows are indicated by arrows. This results in a milling action of the particles within the circular milling chamber 12. The air flow through the nozzles is controlled to adjust milling action within the chamber. The particles are milled to a desired diameter size and then are carried out to an air exhaust port 15 in the center of the milling chamber. A separator 6 directs the milled particles so that they are deposited in a collector bottle 7 while air is exhausted through the air outlet tube port 8.

Crystalline monocomponent porcine insulin (obtained from Novo, Bagarvaerd, Denmark) was then bound to the particles using a solution comprising 8% by weight hydroxypropylcellulose and 0.005M sodium lauryl sulfate, 0.005M triethylamine HCl and 0.005M citric acid. The particles with the insulin bound to their surfaces were then coated with a solution comprising 6% by weight polyethylene glycol monostearate (EMANON-3199 obtained from KAO, Tokyo, Japan) to form a lipid coating approximately 0.1 micron thick. An enteric coating solution was then prepared by dissolving 4.5 w/w% hydroxymethylcellulose phthalate (HPC-55), 0.5 w/w% shellac (Shin-Etsu Chemical, Japan) and 0.5 w/w% polyethylene glycol 6000 (Shin-Wha Yakuhin, Japan) in a solution comprising 47.3 parts by volume dichloromethane and 37.8 parts by volume ethanol. The solution was then diluted with water to an optimum concentration such that the lipid coated particles were then coated with the enteric coating at a thickness of approximately 0.1 microns. Two hundred and fifty mg of the enteric coated particles were then packed by hand into hard gelatin capsules.

The composition was prepared utilizing a modified "Freund" Spir-A-Flow, model SFC-Mini-S 220 V, 60 HZ, 3P (available from Freund International, Tokyo, Japan). The standard Spir-A-Flow was modified as follows. The mesh-holes in the rotor were found to be too big. Accordingly, two additional mesh rings were added. The mesh rings were also oriented so that the particles would not fall through.

The Spir-A-Flow was also modified so that the air being pumped was dried and had all oil particulate removed. The air was dried to 20% absolute humidity. The air flow pressure was also increased to 920 liters per minute and the air flow was oriented so that it was blown up through the base.

Moreover, instead of one air inlet opening the base, four openings were utilized. The openings were oriented in the base at 0°, 90°, 180°, and 270°.

The bag filters and pulsing filters were also cut to one half their length.

Furthermore, instead of one nozzle located at the bottom of the vessel, three nozzles were oriented at the bottom of the vessel. A fourth coating nozzle was also located at the top of the vessel. The bottom nozzles were used for binding and the top nozzle for coating.

Figure 3:
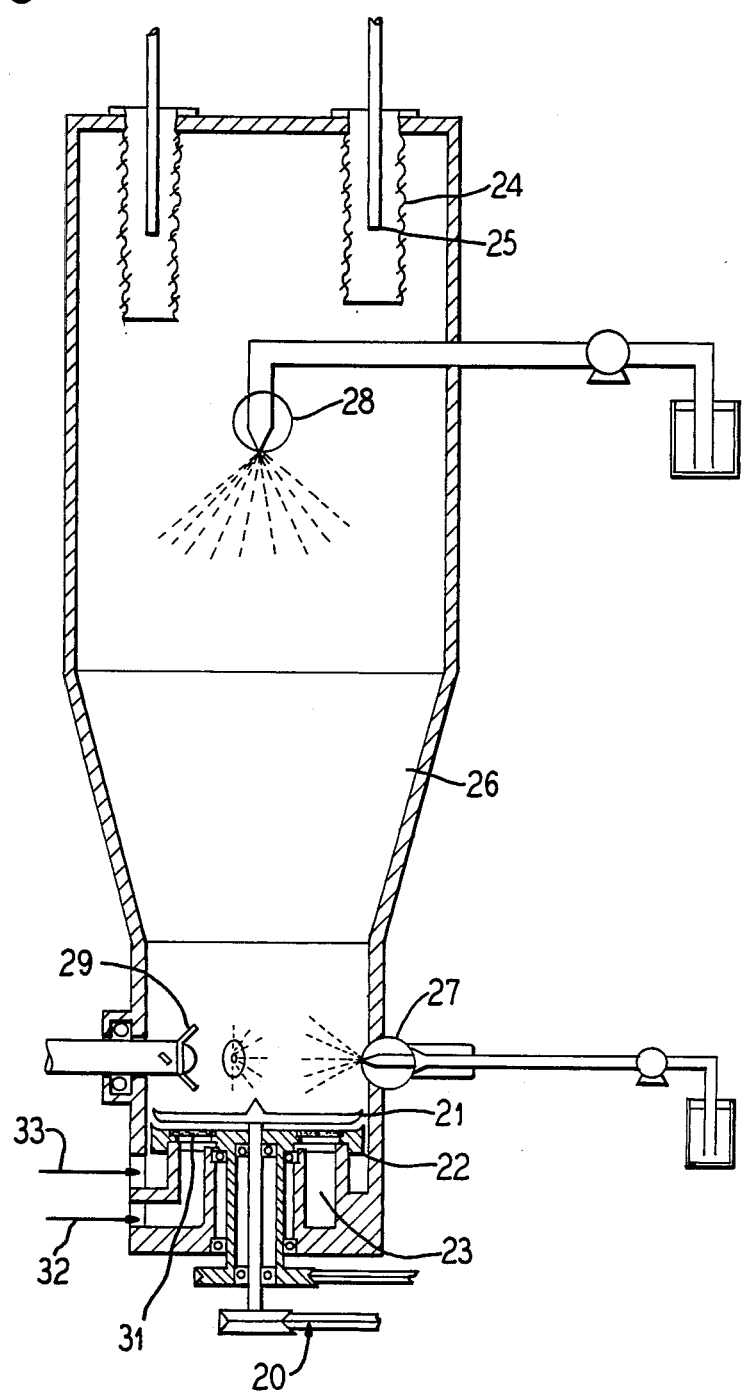
FIG. 3 illustrates a cross-sectional schematic view of a Spir-A-Flow.

FIG. 3 illustrates a Spir-A-Flow apparatus 20. Briefly, the Spir-A-Flow apparatus 20 functions as follows. Particles are placed on the rotating disk 22. The rotating disk 22 includes mesh holes 31. A chopper 29 and agitator 21 cooperate with the disk 22 to form the particles to a given size. The air flow is then turned on and the particles are suspended in the vessel 26. Two types of air flow are generated, slit air and fluid air. Slit air flow enters through aperture 33 while fluid air enters through aperture 32. The suspended particles can then be coated by a binding solution sprayed from the lower nozzles 27. Although only one lower nozzle 27 is illustrated in the modified Spir-A-Flow 20, three lower spray nozzles 27 were utilized. As the particles are coated they fall back to the disk 22. Once all of the particles are coated with the binder the air flow is increased and the coated particles can be coated again, and so forth. As discussed hereinafter, the particles can also be coated by solution sprayed from the upper nozzle 28.

Because of the repeated movements in binding and coating of the powdery particles, the particles are well mixed, wetted, kneaded, and tumbled very efficiently and turn into high quality granules very quickly. A hot air stream through the perforated area of the disk, drys the granules effectively and efficiently. If dusty materials are generated and lifted up to the top, this dust is collected by the bag filters 24. Air jet cleaning nozzles 25 are used to blow the dusty materials collected by the filters back to the disk 22 at the base as necessary.

The rotating disk 22 and chopper 29 combine to form particles having a spherical and smooth surface, with a high mechanical strength, high bulk density and narrow particle size distribution. To create the composition of this example, the solid emulsion-solubilizing agents, surfactants, anti-microbial preservatives were placed into the vessel through an inlet. As the powdery raw materials were placed into the vessel gentle air streams were blown upward, through a perforated parts of the rotating disk and a circumferential gap between the rotating disk and inner wall of the chamber (the vessel). The flow of air prevents the materials from falling down through the gap and perforated parts.

The rotating disk 22, agitator 21, and chopper 29 were started after the raw materials have been inserted. To create the composition of Example 1, the rotor was (and accordingly perforated disk) rotated at a rate of 300 rotations per minute (r.p.m.), the chopper at 2,000 r.p.m., and the agitator rotated at 500 r.p.m. Air streams at a temperature of 32° to 35° C. are passed through the openings in the rotor ("fluid air") at a flow rate of 8 to 10 liters per minute, and through the slit between the rotor and the wall ("slit air") at 7 to 8 L/min. The combined particles were dried for 30 minutes.

A crystalline insulin (Novo Monocomponent Porchin Crystalline Insulin, Batch No. 833115, Lot No. 69195-01) was thoroughly dissolved in a solution containing hydroxypropylcellulose, sodium lauryl sulfate, citric acid, and triethylamine HCl, pH 2.0.

Figure 7:
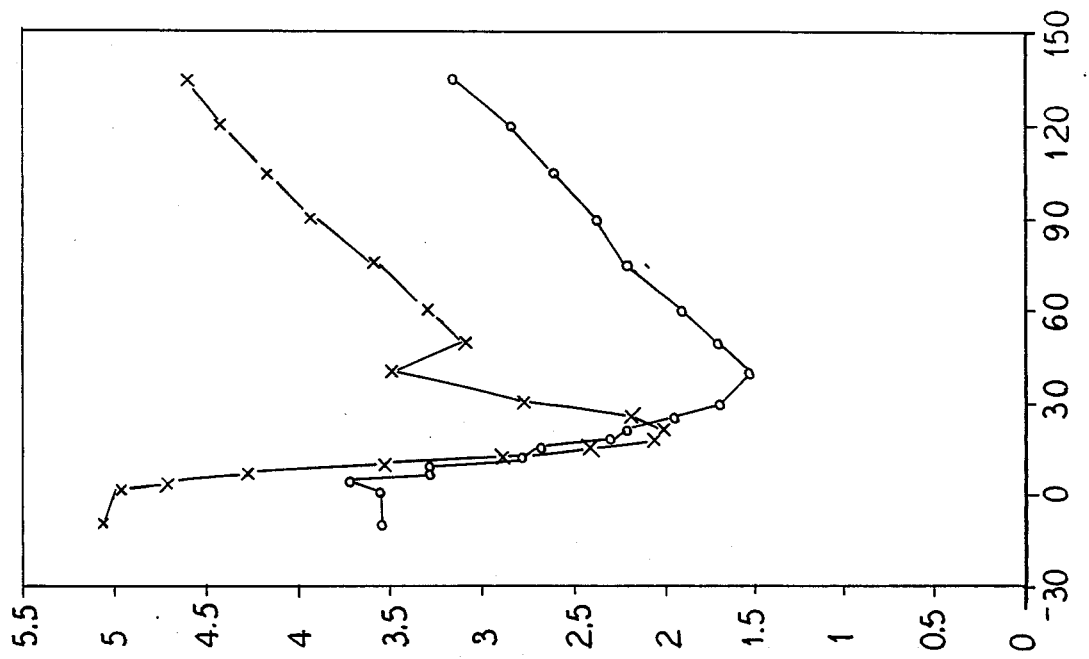
FIG. 7 is a comparison of the venous serum sugar levels of two pigs, one given the composition of Example 1 and one given Actrapid. The venous serum sugar level of the pig given Example 1 is denoted by "o" and the venous serum sugar level of the pig given actrapid is denoted by "x". The x axis is in minutes and the y axis is in millimoles of serum glucose.

While the particles were being blown upward within the wall of the coating and binding apparatus equipment, by the "slit air" and the "fluid air", the binding solution was sprayed as a fine mist through a dual spray nozzle at a spray air pressure of 3.0 Kg per $M^2$ and at an air:flow rate of 10 L/min.

The Insulin-Bound Solid Emulsifying Particles were then coated with a lipid coating comprising a solution of Polyethylene Glycol Fatty Acid Esters (KAO SEKKEN, Japan: EMANON 3199, Lot No. 12744Y) at a spray air-flow rate of 10 L/min and an spray air-pressure of 3.0 Kg/$M^2$.

The above coated Insulin-bound Solid Emulsifying Particles wre then placed into a hard gel capsules, these capsules were then enteric coated.

| | |
|---|---|
| Cholesterol (Fuluka, A.G.; Switzerland; Lot No. 24657-784) | $-6.76 \times 10^{-4}$M |
| Sodium Lauryl Sulfate (Yakuri Kagaku, Japan; S316-06) | $-1.377 \times 10^{-4}$M |
| Triethylamine HCl (Wako Sei-Yaku, Japan) | $-4.089 \times 10^{-6}$M |
| Citric Acid (Yakuri Kagaku, Japan; KA9105) | $-5.965 \times 10^{-6}$M |
| Hydroxypropylcellulose-L (Shin-Wa Yakuhin, Japan; 191184) | $-1.234 \times 10^{-2}$Gm |
| Polyethylene Glycol Fatty Acid Esters (KAO Sekken, Japan; EMANON 3199; 12744Y) | $-1.543 \times 10^{-2}$Gm |
| Insulin (NOVO) | −8 units |

Citric acid is used as an inhibitor of insulin-inactivating enzymes as well as an insulin stabilizer and pH adjuster.

Triethylamine HCl is used as an insulin stabilizer and as an anti-foaming agent.

TEST 1-A

In this test, the oral insuling composition of Example 1 was compared chemically with a sample of Actripid intravenous insulin solution (Novo). One capsule of the oral insulin composition containing 8 international units (I.U.) of Novo monocomponent porchin crystalline insulin prepared according to Example I was dissolved, by sonification using an ultrasonifer for 5 minutes, in water. One-half (½) of the solution—containing 4 I.U. of the oral insulin composition—was analyzed using reverse phase chromotography. 4 I.U. of the Novo actrapid insulin was also analyzed using reverse phase chromotography. The results indicated that both samples contain the same amount of chemically equivalent insulin. (See FIG. 4.)

TEST 1-B

In this test, photomicrographs, using a scanning electron microscope, of the oral insulin composition of Example 1 were taken. The enteric and lipid coatings of the particles were removed by means of a solvent which comprised 47.3 parts, by volume, dichloromethane and 37.8 parts, by volume, ethanol in water. Photomicrographs of the particles at 500× magnification showed relatively small particles (about 5 to 10 microns in average diameter) of insulin and hydroxypropylcellulose binder materials attached to relatively large particles (about 50 microns in average diameter) of cholesterol and sodium lauryl sulfate materials. (See FIG. 5.) At magnification of 300× rod shaped insulin crystals are visible impregnated within the hydroxypropylcellulose particles. (See FIG. 6.)

TEST 1-C

In this test, the oral insulin composition of Example 1 was compared with Actripid intravenous insulin solution (Novo) in a bioassay. Two Yorkshire pigs were fasted overnight and one pig was given 8 I.U. of the Actripid insulin intravenously. The other pig was given an intravenous infusion over a period of 15 minutes of 8 I.U. of the oral insulin composition of Example 1 that had been dissolved into 50 ml of water. Blood was taken from the pair of pigs and the serum sugar levels were measured. The venous serum suger levels of the two pigs decreased by roughly an equal degree although the duration of the hypoglycemic action for the composition of Example 1 was somewhat longer than that of the Actripid insulin. (See FIG. 7.)

TEST 1-D

In this test, the oral insulin composition of Example 1 was compared with Novo monocomponent porcine crystalline insulin and a regular injectable insulin-40 (Tong-Shin Pharmaceutical Co.) in intravenous rabbit bioassays. Three white rabbits, each weighing 1.8 Kg were fasted overnight and were treated with an intravenous infusion over ten minutes of 4 I.U. of either the Novo insulin, the Tong-Shin insulin-40, or an emulsion comprising the oral insulin composition of Example 1. A venous blood sample was collected from the ear vein of each of the rabbits at 30 minutes prior to the insulin infusion and at times 0, 15, 30, 45, 60, 75, 90 and 105 minutes after completion of the infusions.

Figure 8:
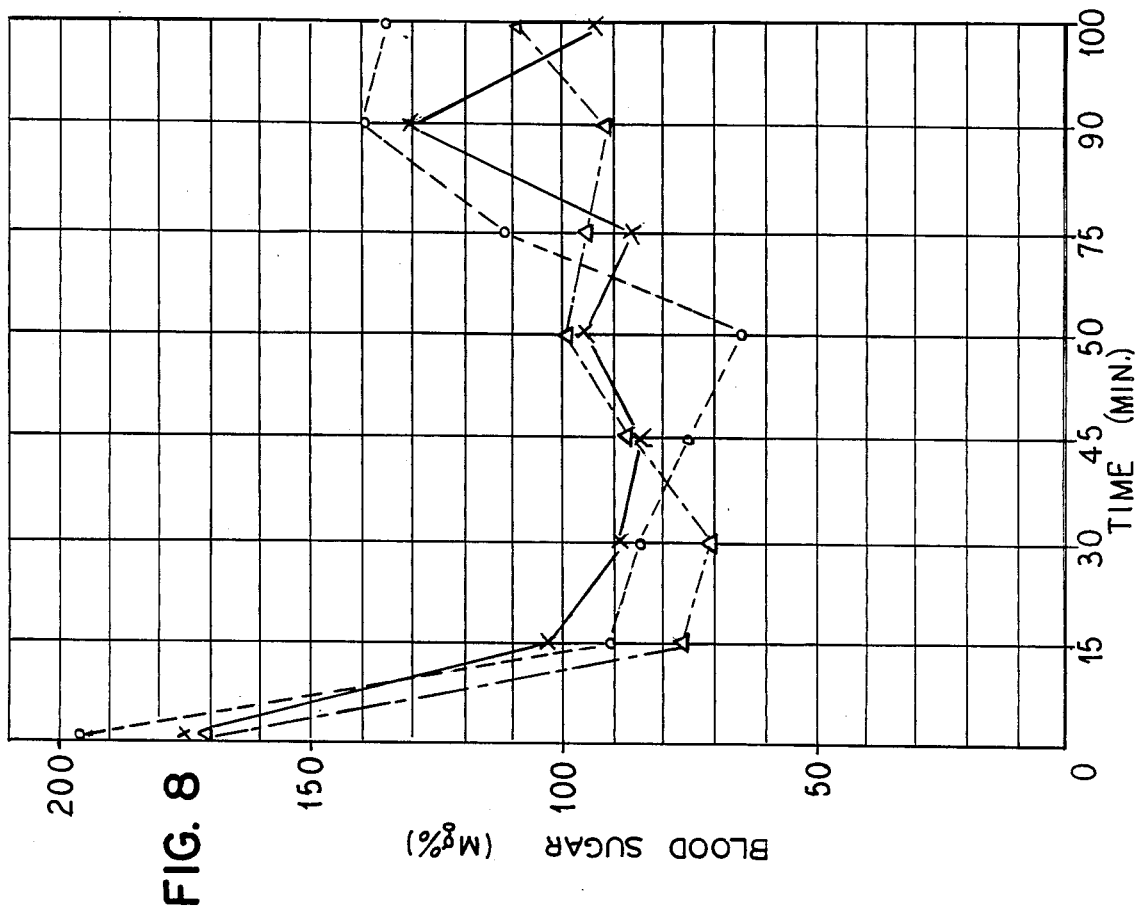
FIG. 8 is a comparison of Tong-Shin insulin, the oral insulin of Example 1, and Novo insulin, pursuant to the test of Test 1-D.

Each of the three forms of insulin exhibited approximately the same hypoglycemic effects with the onset of hypoglycemic action occurring within 30 minutes of the beginning of the infusion. The time of peak hypoglycemic effect of the Novo insulin was determined to be within 30 minutes after completion of the infusion while for the Ton-Shin insulin-40 it was 60 minutes. The emulsion of the oral insulin composition of Example 1 hit its peak of hypoglycemic activity intermediate between the Novo and Ton-Shin insulin. (See FIG. 8.)

TEST 1-E

In this test, the oral insulin composition of Example 1 was administered orally to two healthy male volunteers. Administration of the oral insulin induced hypoglycemic effects comparable to those induced by a subcutaneous injection of an equivalent amount of injectable insulin (Tong-Shin).

Two healthy male volunteers, age 37 and 38, weighing 52 and 54 Kg participated in the study. Each subject received a 16 I.U. dose of the oral insulin composition of Example 1 during the study. Along with the oral insulin composition of Example 1, each participant received two capsules of lipolytic enzymes. Each capsule consisted of:

| | |
|---|---|
| Pancreatic Lipase | 1,000 units |
| Amylase | 7,500 units |
| Protease and | 7,500 units |
| Bile Salts | 40 mg. | per 350 mg capsules, using Corn Starch as the "filler".

The enzyme capsules were made as follows: Pancreatic Lipase was coated with 0.1 to 0.3 microns thick coating of hydroxypropylcellulose and enteric coated with the coating of Example 1. Amylase and Protease were then added. The resultant composition was then coated with 0.1 micron of hydroxypropylcellulose. Bile Salts that had been coated with 0.1 micron of hydroxypropylcellulose was then added to a hard gel capsule with the Pancreatic Lipase resultant product.

At 7:30 am on the day of the trial, each participant consumed a standard breakfast consisting of two fried eggs, two strips of bacon, two slices of toasted dark bread, a tablespoon of butter, and cup of black coffee. The insulin composition of Example 1 was administered orally at 10:00 am to both subjects. The oral insulin was administered in capsules comprising 16 I.U. of Novo crystalline monocomponent porcine insulin. At 12:00 both subjects consumed a standard lunch consisting of 180 gm of beef steak, a tossed green salad with oil and vinegar dressing, a piece of dark bread, and black coffee.

Blood samples were collected from the subject at 10:00, 13:00 and 16:00 and were analyzed for blood glucose levels. The samples indicated that the oral insulin composition exerted a strong hypoglycemic effect upon both subjects after three hours but that after six hours the blood glucose levels had returned to their pretreatment levels.

The blood glucose levels had dropped dramatically for both subjects three hours after the administration of the insulin. At approximately 10:45 the first subject started to complain about having blurred vision, being unable to concentrate and having nausea. By 11:20 the same subject started to complain about cramping and trembling in the arms and legs and cold sweating. The second subject also complained of roughly similar symptoms but of lesser intensity. At 11:30, both subjects were given 250 ml of pure orange juice and the first subject additionally consumed 250 ml of a soft drink.

One week later, both volunteers had the standard breakfast (i.e., the breakfast given on the first day of the test) at the same time. At 10:00 both subjects received a subcutaneous injection of 16 I.U. of Tong-Shin regular injectable insulin-40. At approximately 10:30 both subjects began to experience hypoglycemic reactions which lasted for roughly two hours. Both subjects were served pure orange juice at 11:20 and were served the standard lunch at 12:00. Blood glucose levels measured at 10:00, 13:00 and 16:00 indicated that the injected insulin produced a peak hypoglycemic effect roughly 3 hours after administration and indicated that like the oral insulin composition of Example 1, the effect disappeared by 6 hours after administration (See FIG. 9.)

TEST 1-F

In this test, the oral insulin composition of Example 1 was administered to five individuals suffering from insulin dependent diabetes mellitis (IDDM) and five individuals suffering from non-insulin dependent diabetes mellitis (NIDDM). The IDDM patients were cared for in a hospital setting for a minimum of three days prior to testing and their blood sugar levels were regulated by a proper hospital diet and a series of subcutaneous injections of regular insulin Tong-Shin. The NIDDM patients had their blood sugar levels controlled by a hospital diet and by oral administration of oral hypoglycemic agents such as chloropropamide (Diabinase manufactured by Pfizer Laboratories Division, New York, N.Y.).

On the morning of the first day of testing, a regular breakfast was consumed by each of the patients but the oral hypoglycemic agents and the subcutaneous injections of insulin were withheld from the patients. Instead, the patients received an oral administration of the appropriate dose of the oral insulin composition of Example 1 and two capsules of the lipolytic enzyme composition set forth in Test 1-E. Blood samples were taken from the individuals immediately prior to administration of the oral insulin composition and at two and four hours after administration. These samples were then measured for blood glucose levels. A standardized hospital lunch was served to each patient two hours after administration of the oral insulin composition.

The results of the test are set forth in Table 1.

TABLE 1

| | | | | Average Daily Requirements | | | | | | |
|---|---|---|---|---|---|---|---|---|---|---|
| | | | | Regular Insulin | NPH | Diabinase | Dose Example Composition | Blood Glucose Levels (Mg %) | | |
| Subject | Disease Type | Sex | Age | (I.U.) | (I.U.) | (Mg.) | (I.U.) | 0 hrs. | 2 hrs | 4 hrs |
| A | IDDM | M | 49 | 40 | 80 | 0 | 24 | 252 | 103 | 140 |
| B | IDDM | M | 59 | 60 | 145 | 0 | 32 | 227 | 153 | 220 |
| C | IDDM | M | 54 | 30 | 30 | 0 | 32 | 201 | 137 | 177 |
| D | IDDM | M | 48 | 90 | 110 | 0 | 32 | 199 | 140 | 197 |
| E | IDDM | F | 44 | 40 | 70 | 0 | 32 | 203 | 163 | 212 |
| F | NIDDM | F | 41 | 0 | 0 | 250 | 32 | 290 | 170 | 117 |
| G | NIDDM | F | 57 | 0 | 0 | 250 | 32 | 276 | 201 | 109 |
| H | NIDDM | M | 52 | 0 | 0 | 250 | 24 | 189 | 188 | 132 |
| I | NIDDM | M | 63 | 0 | 0 | 250 | 24 | 156 | 121 | 130 |
| J | NIDDM | F | 65 | 0 | 0 | 375 | 32 | 241 | 171 | 120 |

As shown in Table 1 the blood glucose levels of all patients fell significantly between administration of the oral insulin composition and two hours later. But, the glucose levels of the IDDM patients rose again sharply between two and four hours, and in three of the five patients roughly equalled or exceeded the pretreatment levels. On the other hand, the blood glucose levels of those suffering from NIDDM continued to decrease between two and four hours in four of the five patients. In the fifth patient, the blood glucose level rose between two and four hours but did not approach the pretreatment level.

EXAMPLE 2

In this example, a prolonged action oral insulin composition was made according to the general method of Example 1. Particles comprising cholesterol, sodium lauryl sulfate and methyl and propyl-parabens were produced and were coated with particles comprising Novo monocomponent porcine insulin bound with hydroxpropylcellulose (40 gm of hydroxpropylcellulose in 600 ml of water; 6.07% solution), sodium lauryl sulfate, triethylamine HCl, and citric acid. These particles with insulin bound to their surfaces were then coated with polyethylene glycol monostearate to form a lipid coating around the particles of approximately 0.3 microns thick in contrast to the approximately 0.1 micron thick coating of the composition of Example 1. The particles were then coated with an enteric coating comprising the same materials used for the composition of Example 1 at a coating thickness of approximately 0.1 microns.

TEST 2-A

In this test, the prolonged action oral insulin composition of Example 2 was administered to three subjects suffering from IDDM and three subjects suffering from NIDDM (subjects A, D, E, G, I and J from Test 1-F). On the morning of the study, a regular breakfast was consumed by each of the subject but the subjects were denied the oral hypoglycemic agents and the subcutaneous insulin injections that were a part of their normal therapy. Instead, they were treated with orally administered doses of the composition of Example 2 and two capsules of the lipolytic enzyme composition set forth in Test 1-E. Blood samples were taken at the time of the administration of the oral insulin composition and at various times thereafter. A standard hospital lunch was served to the subjects four hours after administration of the insulin composition.

Analysis of the blood glucose levels of the various samples shows that the compositions of Example 2 produce a more prolonged hypoglycemic effect than those of Example 1. The compositions with the thicker lipid and enteric coatings produced peak hypoglycemic effects after 4 to 6 hours and had effects lasting up to 7 hours, which was the entire duration of the study. (See Table 2.)

TABLE 2

| | | | | Average Daily Requirements | | | | | |
|---|---|---|---|---|---|---|---|---|---|
| | | | | Dose Example Composition | Blood Glucose Levels (Mg %) | | | | |
| Subject | Disease Type | Sex | Age | (I.U.) | 0 hrs | 2 hrs | 3 hrs | 4 hrs | 6 hrs | 7 hrs |
| A | IDDM | M | 49 | 32 | 274 | 240 | — | 145 | 126 | 132 |
| D | IDDM | M | 48 | 40 | 277 | 230 | — | 135 | — | 168 |
| E | IDDM | F | 44 | 48 | 285 | 184 | — | 126 | 118 | 126 |
| G | NIDDM | F | 57 | 32 | 301 | 306 | — | 109 | 112 | 200 |
| I | NIDDM | M | 63 | 24 | 270 | 130 | — | 114 | 129 | — |
| J | NIDDM | F | 65 | 32 | 252 | — | 135 | 122 | — | 140 |

TEST 2-B

In this test, comparative tests were conducted on the oral insulin composition of Example 1 and the prolonged action oral insulin composition of Example 2. Three IDDM patients and three NIDDM patients were administered either the composition of Example 1 or the composition of Example 2 on alternate days along with two capsules of the lipolytic enzymes set forth in Test 1-E. Two capsules were given for each oral insulin dose. Each subject fasted overnight and was not served breakfast and was also denied their normal anti-diabetic therapeutic agents. Blood glucose levels of each subject were tested at the time of the administration of the oral composition and at various times thereafter.

The results of the administration to the IDDM subjects of the compositions of Example 1 and 2 show that the composition of Example 1 produced a strong hypoglycemic effect within two hours of the administration but that blood glucose levels returned to approximately their baseline levels after four hours. The compositions of Example 2, however, demonstrated a more gradual effect and did not produce their peak hypoglycemic effect until after four to six hours. Even after 7 hours, however, they produced a pronounced hypoglycemic effect.

The results of administration to the NIDDM subjects show that differences between the two compositions are less distinct. The peak hypoglycemic action for both compositions appears to occur after about 4 hours although the composition of Example 2 may have a more prolonged action than that of Example 1. Both compositions produced a more prolonged period of "normoglycemic" condition in the NIDDM subjects than in the IDDM subjects.

It is suggested that the shorter duration of the hypoglycemic effect of the composition of Example 1 in IDDM patients may be due to the fact that insulin in the composition is released at a faster rate than that of the composition of Example 2 but that it is also inactivated at a faster rate in IDDM patients because of the présence of anti-insulin antibodies that are often found in IDDM patients. (See FIGS. 10 and 11.)

EXAMPLE 3

In this example, an alternative prolonged action oral insulin composition was produced according to the basic procedure of Example 1. Particles having an average diameter of about 50 microns were prepared from a mixture of cholesterol, sodium lauryl sulfate, and methyl and propylparabens. Novo crystalline monocomponent insulin was then bound to the particles with binders comprising hydroxpropylcellulose, sodium lauryl sulfate, triethylamine HCl, and citric acid. The particles with the insulin bound to their surfaces were then coated twice with a polyethylene glycol monostearate coating each of which was 0.15 microns thick. The particles with the double lipid coatings were then coated with an enteric coating according to the composition of Example 1 at a thickness of 0.1 microns.

TEST 3-A

In this test, the prolonged action insulin compositions of Example 3 were administered to three subjects suffering from IDDM. Treatment was according to the general protocol followed in clinical test 1 wherein the subjects fasted overnight and were denied their normal hypoglycemic therapies. The subjects consumed a standard hospital breakfast and were administered an oral dose of the insulin composition of Example 3 and two capsules of lipolytic enzyme composition set forth in Test 1-E. The subjects consumed a standard hospital lunch 3 hours after administration of the oral insulin composition of Example 3.

Blood glucose levels of the subjects were measured from venous blood samples collected from the subject at various times following administration of the oral insulin. The data which is presented in table 3 indicates a prolonged hypoglycemic effect with the peak hypoglycemic effect occurring between 4 and 6 hours but with hypoglycemic activity lasting for as long as 9 hours.

One subject suffering from NIDDM was also treated with the composition of Example 3 and lipolytic enzymes set forth in Test 1-E. This subject fasted overnight prior to the test as well as throughout the duration of the test. The NIDDM subject was treated at 10:00 AM and her blood glucose level continued to fall over the entire five and one half hour duration of the test.

TABLE 3

| Subject | Disease Type | Sex | Age | Average Daily Requirements Dose Example Composition (I.U.) | Blood Glucose Levels (Mg %) | | | | |
|---|---|---|---|---|---|---|---|---|---|
| | | | | | 0 hrs | 2 hrs | 3 hrs | 6 hrs | 8 hrs | 7 hrs |
| C | IDDM | M | 54 | 32 | 191 | — | 208 | 144 | — | 163 |
| K | IDDM | F | 20 | 32 | 291 | — | 138 | 268 | — | 193 |
| L | IDDM | M | 31 | 32 | 180 | 181 | — | 149 | 176 | — |
| M | NIDDM | F | 58 | 48 | 389 | — | 241 | 159 | — | — |

EXAMPLE 4

In this example oral insulin having a composition similar to that of the oral insulin composition of Example 1 was produced. The composition of Example 1 was varied by varying the lipid coating. The lipid coating was varied so that in addition to polyethylene glycol monostearate, phosphotidylephosphate (an amount sufficient to make a final concentration of $0.046 \times 10^{-2}$ gm), phospholipids (an amount sufficient to to make a final concentration of $0.046 \times 10^{-2}$ gm), and cholesterol (an amount sufficient to make a final concentration $2.628 \times 10^{-4}$ mol) were added to the lipid coating materials. This lipid coating was coated onto the insulin and particles at a thickness of 0.3 microns. 240 mg of the oral insulin product was then packed by hand into a hard gel capsule. The gel capsule was coated with the enteric coating of Example 1.

EXAMPLE 5

In this example oral insulin similar to the oral insulin composition of Example 3 was produced. The oral insulin is modified to the extent that a combination of cholesterol-arginine HCl was substituted for the cholesterol of Example 3. The cholesterol arginine HCl provides a composition that mimics the low density lipoprotein compositions in vivo. Also, the lipid coating materials were changed. After coating the composition with a lipid coating similar to that of Example 4 at a thickness of 0.15 microns, a second lipid coating is applied. The second lipid coating includes oleic acid (an amount sufficient to make a final concentration of $8.776 \times 10^{-6}$ mol), and tromethan (an amount sufficient to make a final concentration of $8.764 \times 10^{-6}$ mol) as a "vulcanizer" or "plasticizer" of the liquid coating membranes.

Briefly, the oral insulin of this example consists of "lower-density lipoprotein-like" solid emulsifying agent as the base. NOVO Monocomponent Crystalline Porchin insulin was bound to the emulsifying agent and the resultant product was coated with a 0.1 micron thick hydroxypropylmethylcellulose water soluble coating, which was then coated twice with the lipid coating materials to a final membrane thickness of 0.3 microns (0.15 microns per layer of the lipid coating), a "stabilizer tromethan" was added, and the product was then packed by hand into a hard gel capsule (so that each capsule contains 240 mg of the composition). The capsule was then coated with the enteric material of Example 1. The water soluble coating allows the insulin-cholesterol arginine HCl to be coated with a lipid coating.

TEST 5-A

The bioavailability of insulin and its corresponding hypoglycemic effects of Example 4 and Example 5 oral insulin preparations were studied in a group of IDDM and NIDDM patients. Example 4 oral insulin was also studied in two normal, healthy male volunteers. In all of the tests set forth in 5-A, the subjects received with each dose of oral insulin two capsules of the lipolytic enzyme of Test 1-E.

At least 12 or 24 hours prior to the study the patients normal anti-diabetic therapeutic agents were withheld from the patients. After overnight fasting and fasting throughout the entire period of the study, Example 4 or Example 5 oral insulin preparations were orally administered.

A venous sampling catheter was placed into a vein, usually at the antecubital vein, and blood samples were drawn at time 0, 1.0, 1.5, 2.0, 2.5, 3.0, 4.0 and/or 5.0 hours after the drug administration. Serum glucose was measured on a Gilfordx400, and serum insulin was analyzed by using an Immuno-Enzymatic o-Phenylendiamine (OPD) method and Insulin-B test kit of WAKO (Japan). All measurements were made in duplicate.

As stated above, two healthy male volunteers ages 38 and 31 years participated in the study. One subject received the oral insulin of Example 4 twice over a two week period, once each week, receiving 0.20 and 0.27 IU per Kg of the oral insulin. The serum glucose level of the subject decreased from a base line average 111.0 mg/dl to an average of 80.5 mg/dl at 3-hour from the time of drug administration. Serum insulin level was peaked to 20 micro-U per ml occurring at 1.5 hours after the drug ingestion on both occasions. At 45 minutes after administration of the oral insulin, the subject complained of blurred vision, cold sweating, irritability, and inability to concentrate.

The second volunteer received 10 IU of regular injectable insulin-40 (of Tong Shin Pharm. Co. of Seoul, Korea), subcutaneously. Typical insulin-induced shock symptoms were observed at 72 minutes after the injection of regular insulin, the serum glucose was 47 mg/dl at that time. He was given a glass of fresh orange juice and serum glucose level rose to about 115 mg/dl within one hour.

Five IDDM Patients have completed all three phases of the study of test 5-A: i.e., they received 10 IU, subcutaneous injection of regular injectable insulin-40 (of Tong Shin Pharm Co. of Seoul, Korea) the first week; they received one single oral dosing of Example 4 (0.544 IU/kg average dose) one week later; and the next week they received 9 consecutive dosings of Example 4 (average dose was 0.544 IU/kg), given at 6-hour intervals.

The Oral Insulin Example 4 was given to a total of 8 IDDM patients (10 trials) (two repeated the study) and 7 NIDDM patients (11 trials) (four patients repeated the study).

Seven IDDM Patients completed the study after oral administration of a single dose of the Example 5 oral insulin preparation.

The studies demonstrated that Example 4 oral insulin apparently has a slower onset of action but exhibits a longer duration of "hypoglycemic" action in both IDDM and NIDDM patients, compared to that of the regular insulin. The bioavailability of insulin of the composition Example 4 was about 3 times that of the regular insulin; however, by adjusting the insulin dosage, it was about the same (see Table 4).

The studies also demonstrated that the insulin composition of Example 5 produced an onset of hypoglycemia as well as had an overall duration of hypoglycemia that grossly resembled that observed after the subcutaneous injection of regular insulin. The bioavailability of insulin was greater for the oral ingestion of Example 5 than that of Example 4.

TABLE 4
BIOAVAILABILITY OF INSULIN AND HYPOGLYCEMIC EFFECTS AFTER ORAL EXAMPLE 4 & 5 VS. REGULAR INSULIN s.c. INJECTION

| PREPARATIONS | DOSE (IU/Kg) | SERUM GLUCOSE (mg/dl) | | | | | SERUM INSULIN (micro-U/ml) | | | | | |
|---|---|---|---|---|---|---|---|---|---|---|---|---|
| | | $C_0$ | $C_{min}$ | $T_{C-min}$ | $T_{100}$ | $dC/dT$ | $I_0$ | $I_{max}$ | $T_{I-max}$ | $T_{I-0}$ | $dI/dT$ | AUC |
| Regular Insulin S.C. Injection | 0.172 | 271 | 94.5 | 4.0 | 2.1 | 59.16 | 8.0 | 20.3 | 1.5 | 4.8 | 38.29 | 305.3 |
| EXAMPLE 4 Oral 1st Dose | 0.544 | 221 | 95.0 | 5.0 | 4.7 | 27.02 | 7.8 | 57.9 65.2* | 1.5 3.0* | 7.2 | 60.01 | 935.7 |
| EXAMPLE 4 Oral 9th Dose | 0.556 | 250 | 78.5 | 5.0 | 3.6 | 37.78 | 64.0 | 121.0 | 1.0 | 8.2 | 72.43 | 1071.8 |
| EXAMPLE 4 Oral 1st Dose in 8 IDDM | 0.535 | 265 | 140 | 5.0 | 6.2 | 32.3 | — | — | — | — | — | — |
| EXAMPLE 4 1st Oral Dose in 7 NIDDM | 0.338 | 231 | 162 | 5.0 | 8.4 | 15.6 | | | | | | |
| EXAMPLE 5 Oral 1st-Fasting | 0.649 | 237 | 98.9 | 3.0 | 2.5 | 59.08 | 13.9 | 185.0 | 2.0 | 7.8 | 76.38 | 1229.4 |
| EXAMPLE 5 | 0.4165 | 192 | 108 | 5.0 | 5.3 | 29.50 | — | — | — | — | — | — |

TABLE 4-continued

BIOAVAILABILITY OF INSULIN AND HYPOGLYCEMIC EFFECTS AFTER ORAL EXAMPLE 4 & 5 VS. REGULAR INSULIN s.c. INJECTION

| PREPARATIONS | DOSE (IU/Kg) | SERUM GLUCOSE (mg/dl) | | | | | SERUM INSULIN (micro-U/ml) | | | | | |
|---|---|---|---|---|---|---|---|---|---|---|---|---|
| | | $C_O$ | $C_{min}$ | $T_{C-min}$ | $T_{100}$ | $dC/dT$ | $I_O$ | $I_{max}$ | $T_{I-max}$ | $T_{I-O}$ | $dI/dT$ | AUC |
| Oral 1st-Postprendial | | | | | | | | | | | | |

$C_O$ = Base value of Serum Glucose;
$C_{min}$ = Minimum value of glucose;
$T_{c-min}$ = Time of observing the minimum glucose level;
$T_{100}$ = Time to reach 100 mg/dl of g; serum gluclose;
$dC/dT$ = The rate of reduction in Serum Glucose levels.
$I_O$ = The base value of Serum Insulin;
$I_{max}$ = Maximum value of insulin;
$T_{I-max}$ = Time to reach the maximum Serum insulin level;
$T_{I-O}$ = The time to reach the base value of Serum Insulin level;
$dI/DT$ = The rate of rise of serum insulin level;
AUC = The area-under the serum insulin level curve over the (study) time period.
(*Double peaking in the serum insulin levels).

EXAMPLE 6

The composition of Example 5 was produced by bonding insulin (novo monocomponent) with cholesterol-sodium lauryl sulfate particles as described in Example 1. The Insulin-bound Solid Emulsifying Particles were then coated with a coating solution containing polyethylene glycol fatty acid esters and Yolk Lecithin with 5% Phosphatic Acid (in an amount sufficient so that the final product of 350 mg capsule to contain $0.309 \times 10^{-2}$ GM). Yolk Lecithin containing 5% of Phosphatic Acid dissolved in ethanol was used (SIGMACHEMICAL, St. Louis, Mo.).

TEST 6

Controlled studies in a group of IDDM and NIDMN patients were conducted by a Korean investigative team and a United States investigative team in Korea. The Patients were given a single oral dose of the composition of Example 6. The Korean investigative team's blood test were analyzed in Korea and at the same laboratory in the United States as the United States investigative team's tests. Some of the patients were also given ten (10) IU of regular injectable insulin (Tong-Shin) on alternate days. Each patient fasted during the study and the night before. All other forms of diabetic therapy were withheld from the patients. Serum samples were analyzed for the serum glucose levels. The results (see FIGS. 12–21) illustrate that the composition of Example 6 is an orally active insulin in both IDDM and NIDDM patients. Moreover, the results illustrate that both laboratories had similar results.

Figure 9:
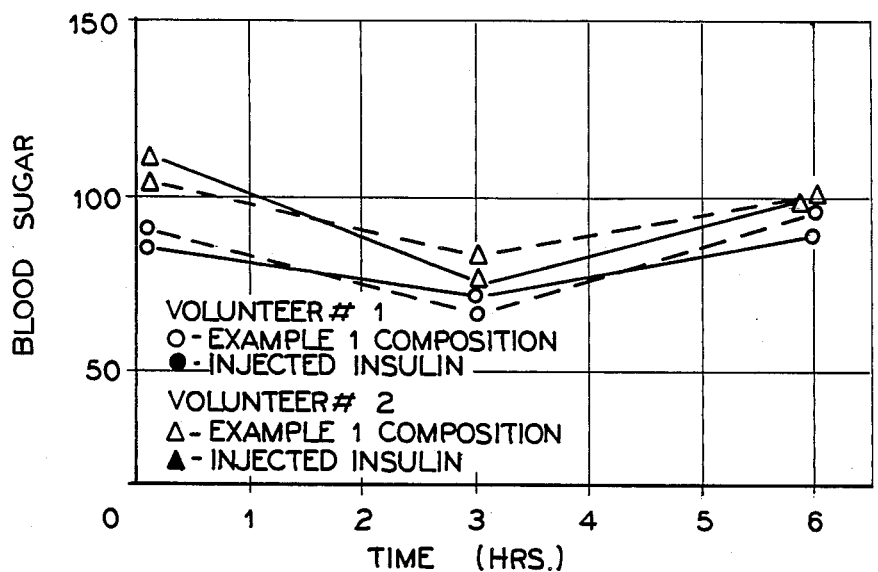
FIG. 9 is a comparison of the oral insulin of Example 1 and regular injected insulin pursuant to Test 1-E.
Figure 10:
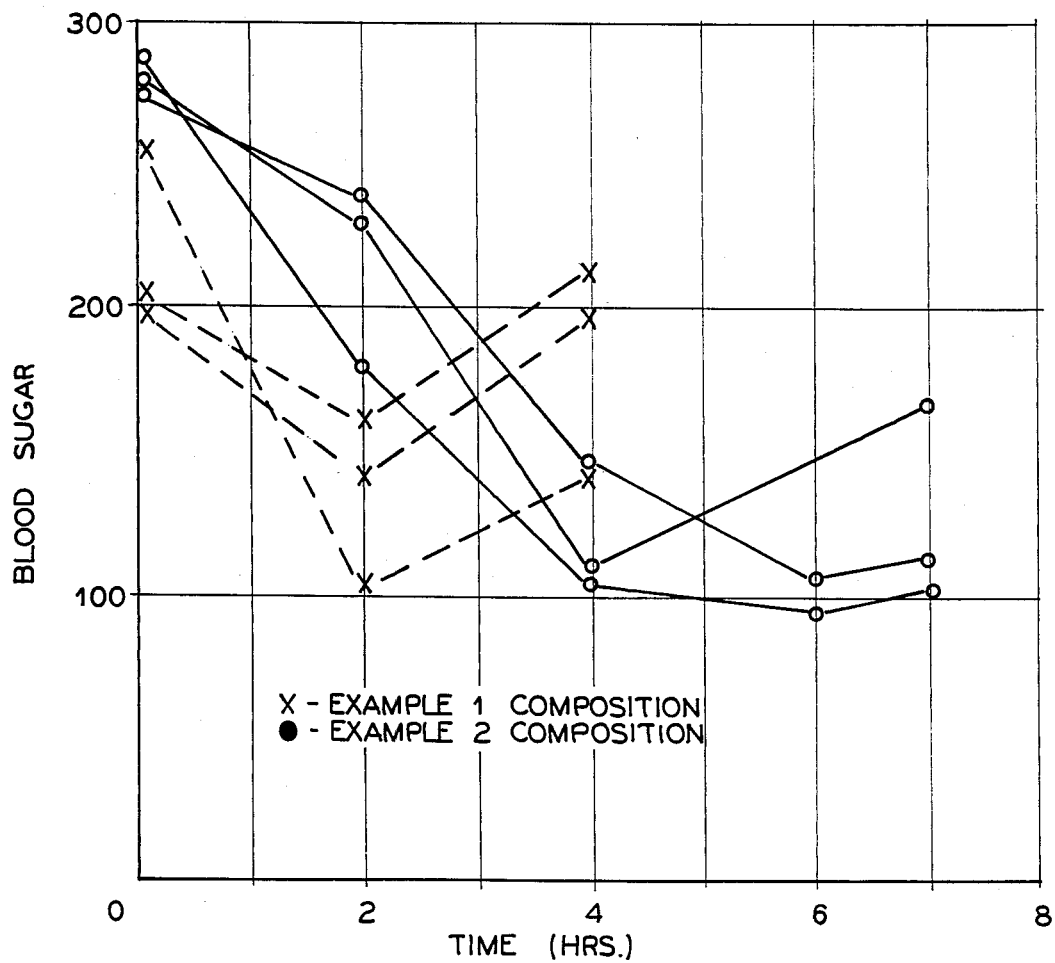
FIG. 10 is a comparison of the oral insulin of Example 1 and oral insulin of Example 2 pursuant to the Test 2-B.

Referring to FIGS. 12–21, the solid lines are tests conducted by the Korean investigative team and the broken lines are the tests conducted by the United States investigative team. The x axis is time (hrs) and the y axis is blood glucose mg/dl. FIG. 9 illustrates the results of a female age 46 given 6 capsules of Example 6. In FIG. 10, the subject (38 year old NIDDM male) was given 10 units regular injected insulin denoted as x, and then 6 capsules (24 units) of Example 6.

Figure 11:
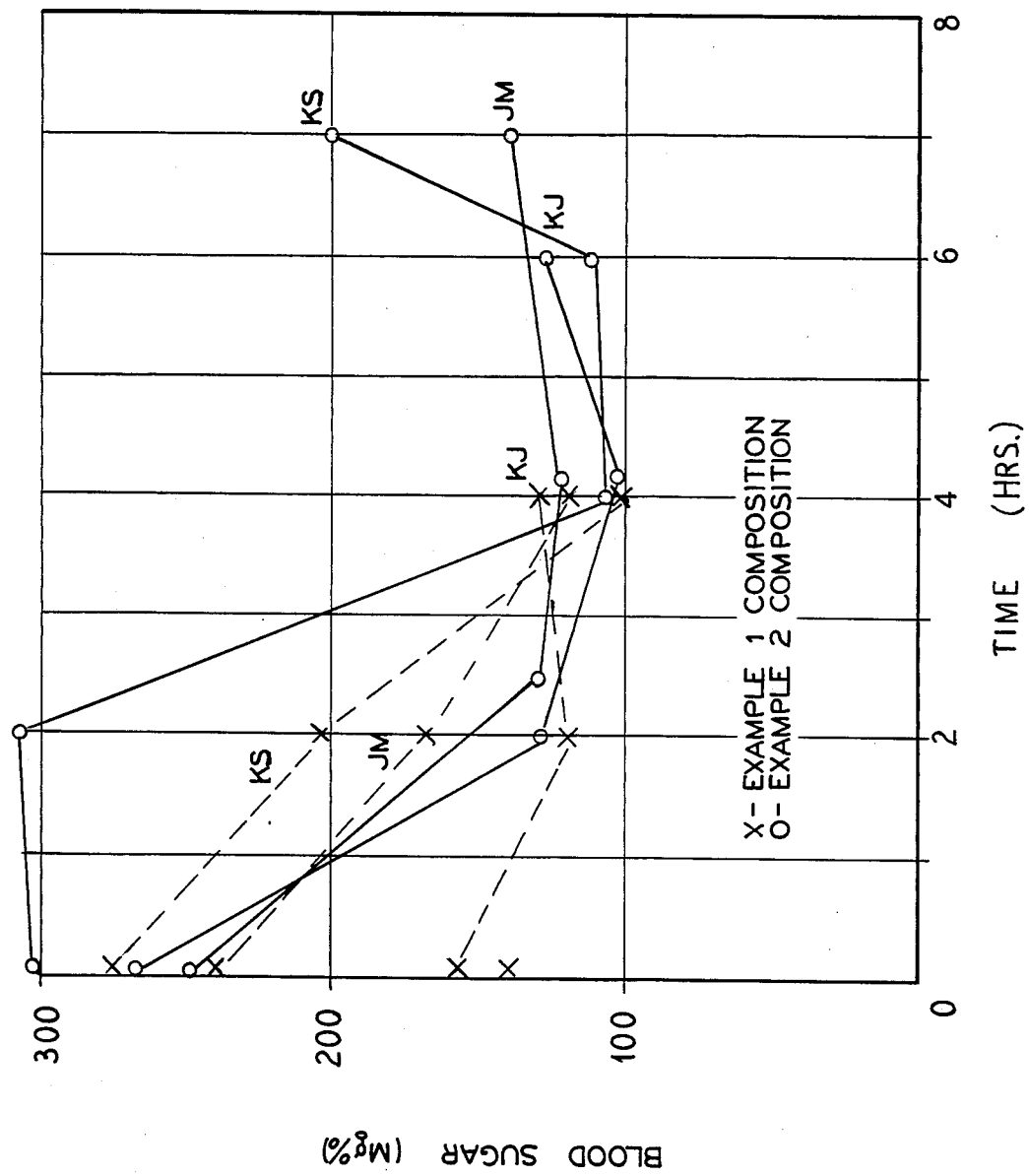
FIG. 11 is a comparison of the oral insulin of Example 1 and oral insulin of Example 2 pursuant to the Test 2-B.

In FIG. 11, the subject, a 47 year old IDDM male was given 10 units of injected insulin, denoted by a ([]), and on day 2, 6 capsules (24 units) of Example 6 (x). In FIG. 11, the subject a IDDM 45 year old male, was given 10 units of injectable insulin ([]) and on day 2, 8 capsules (32 units) of Example 6 (x).

Figure 13:
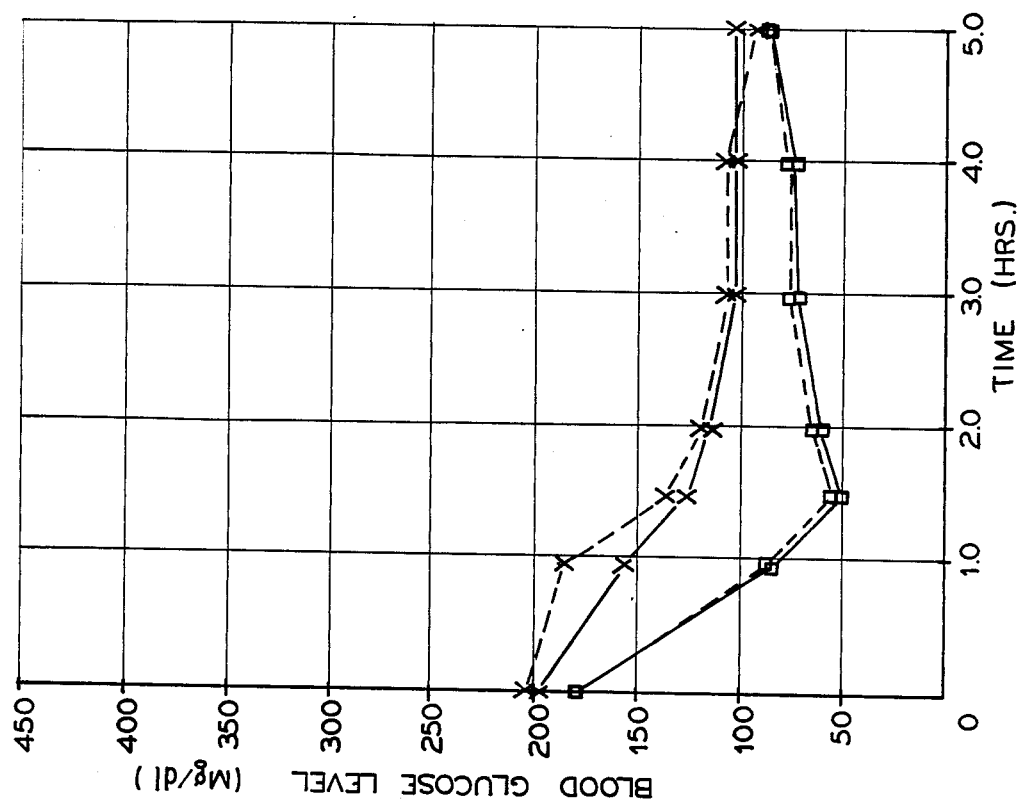
FIG. 13 is a comparison of injectable insulin versus Example 6.
Figure 12:
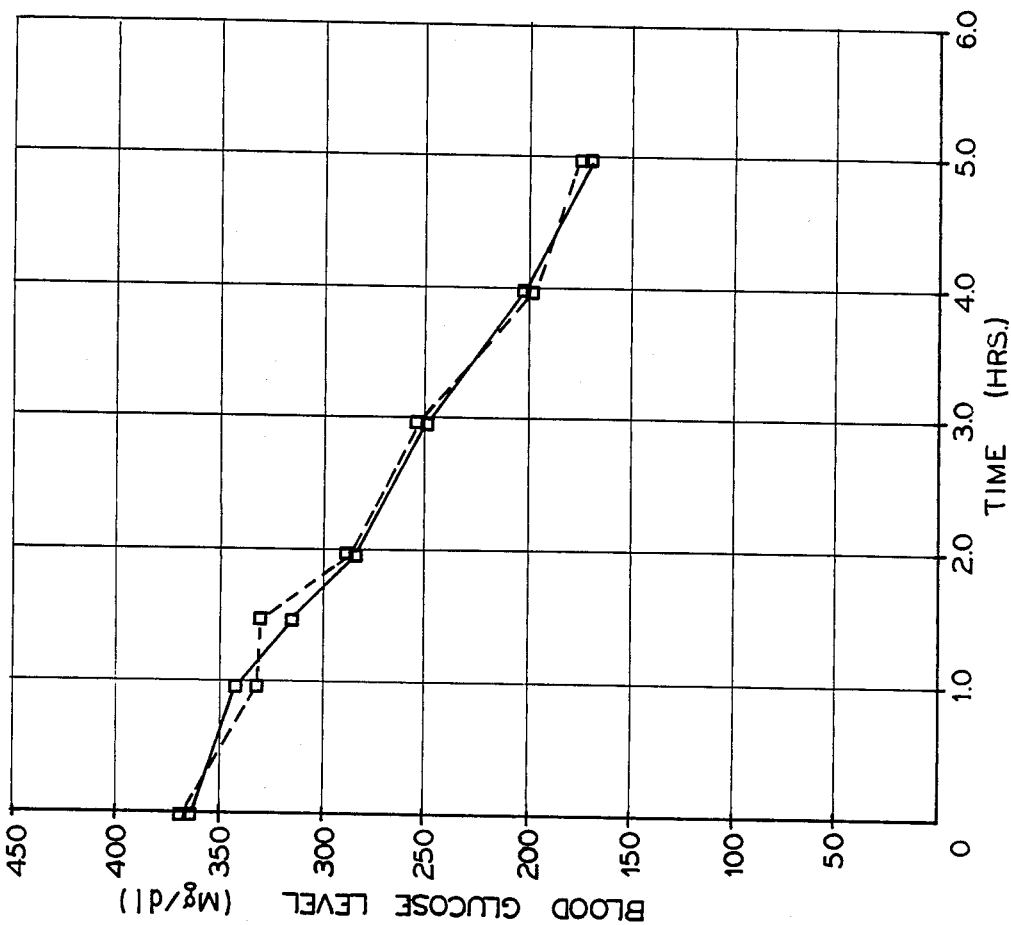
FIG. 12 illustrates the effect of Example 6 on blood glucose levels.
Figure 15:
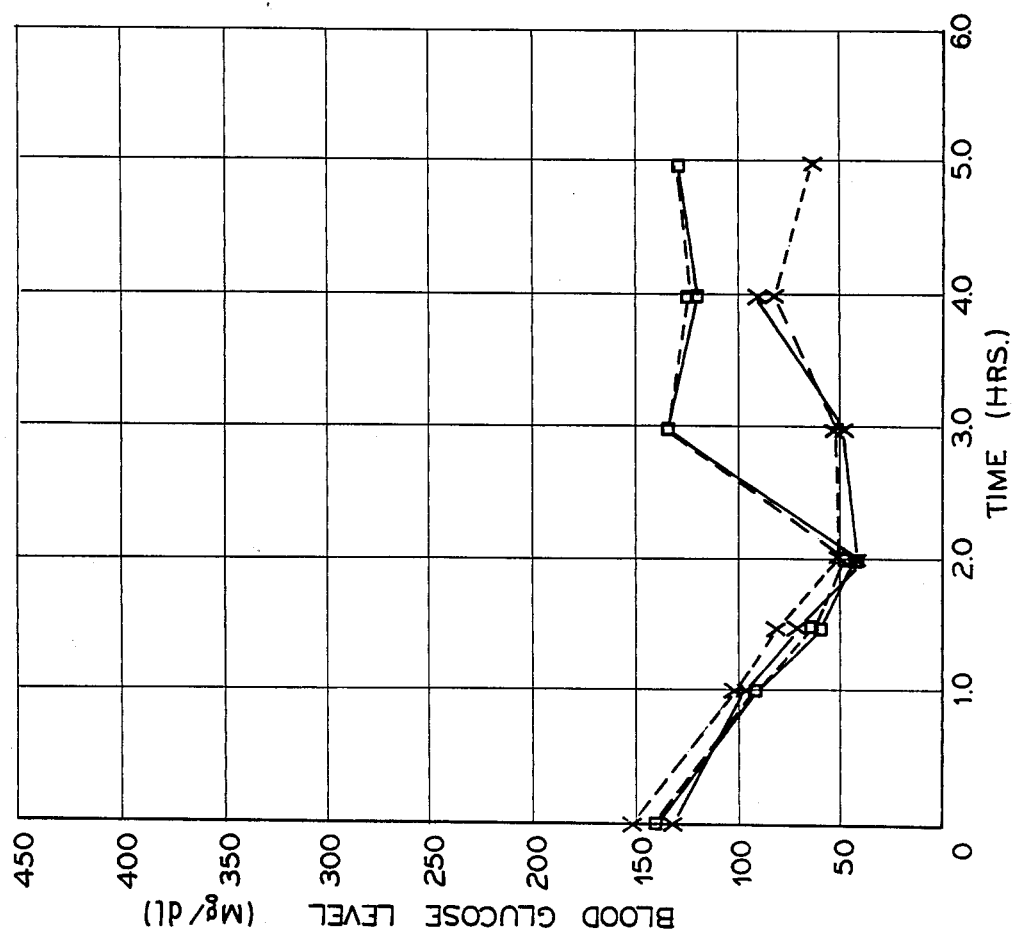
FIG. 15 is a comparison of injectable insulin versus Example 6.
Figure 14:
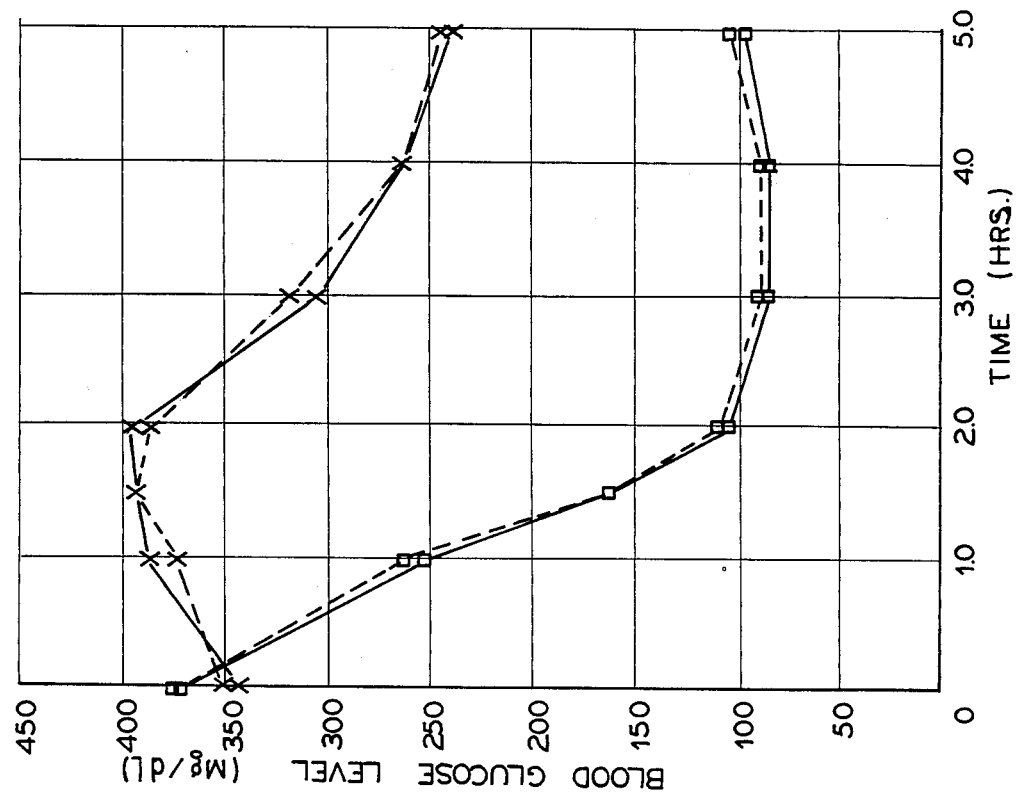
FIG. 14 is a comparison of injectable insulin versus Example 6.
Figure 17:
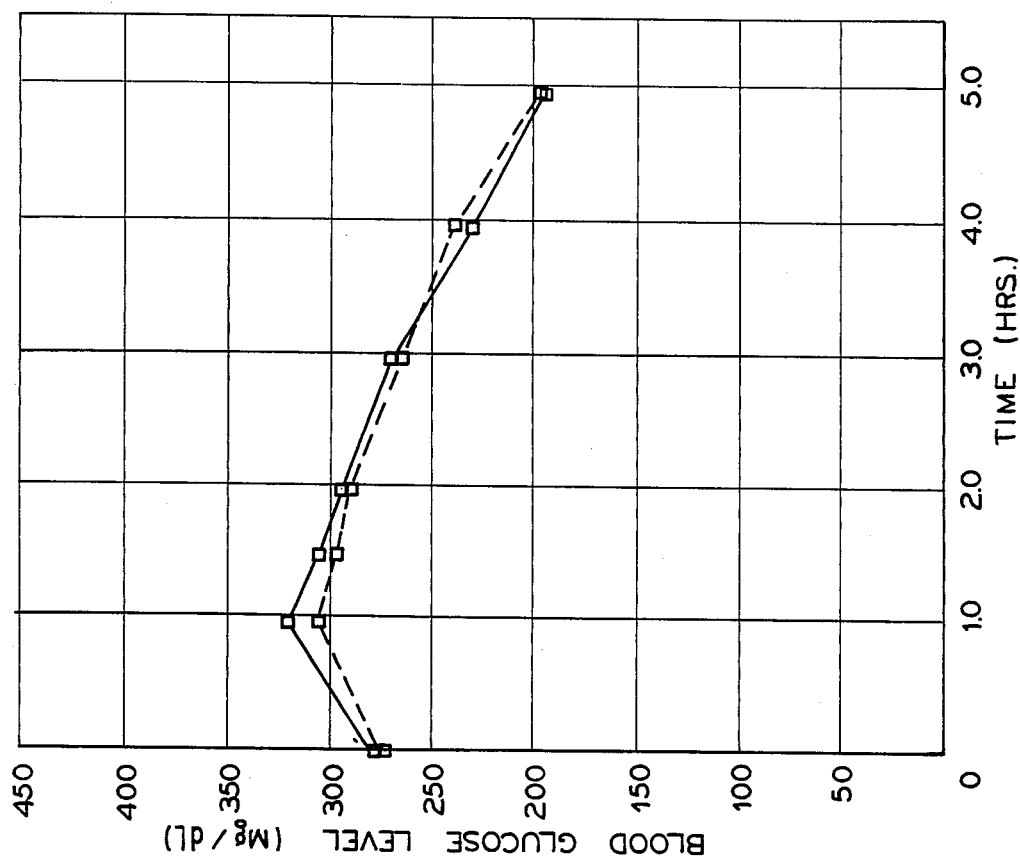
FIG. 17 illustrates the effect of Example 6 on blood glucose levels.
Figure 16:
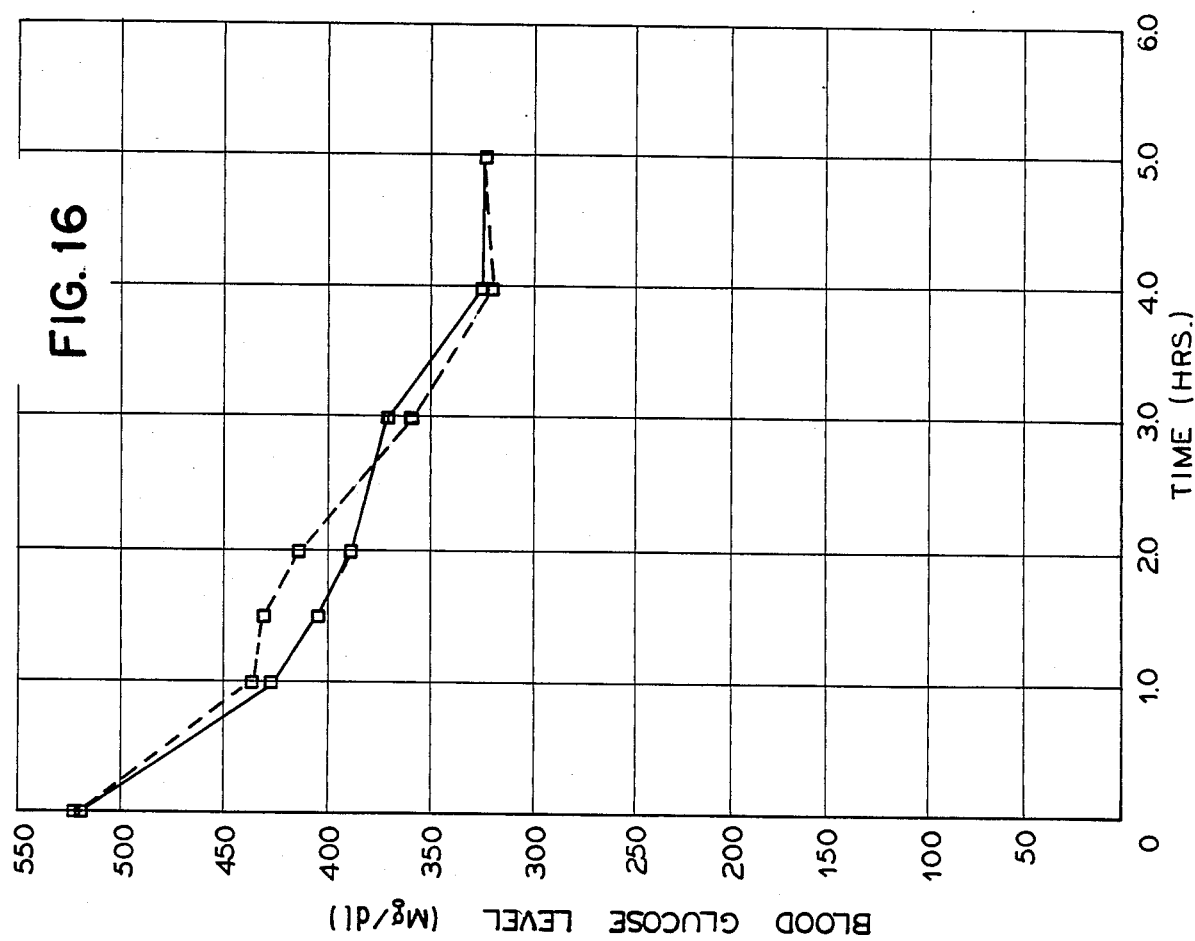
FIG. 16 illustrates the effect of Example 6 on blood glucose levels.
Figure 19:
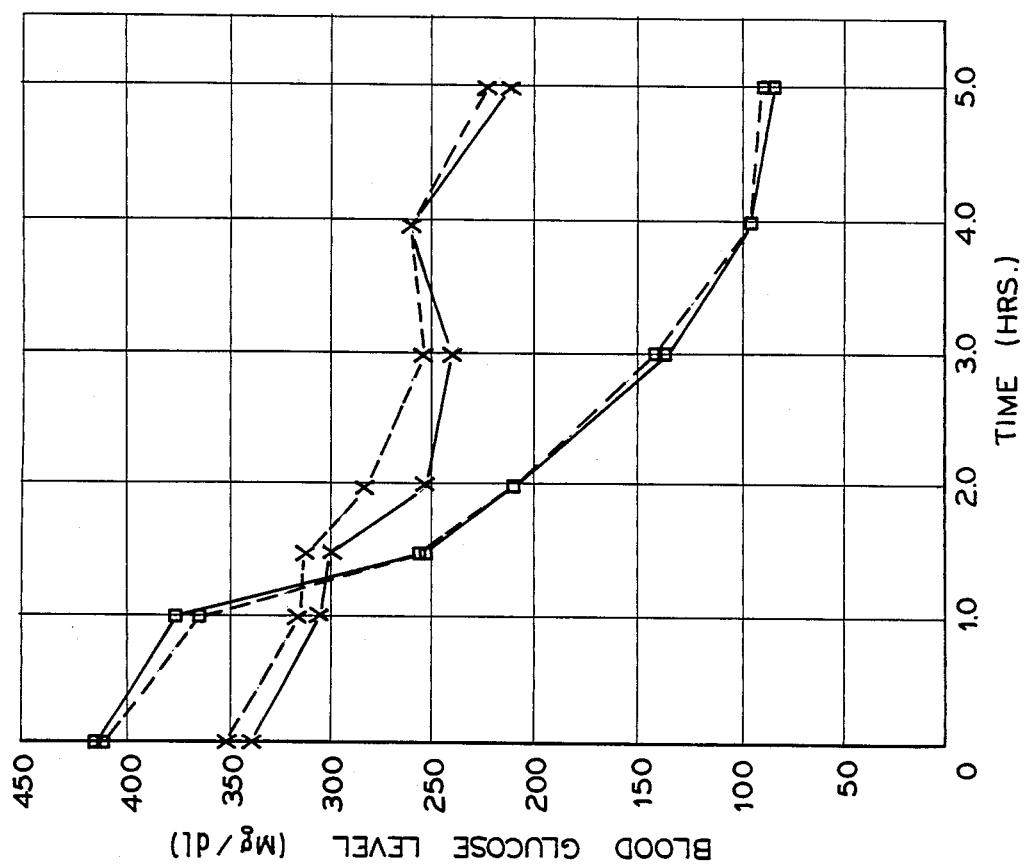
FIG. 19 is a comparison of injectable insulin versus Example 6.
Figure 18:
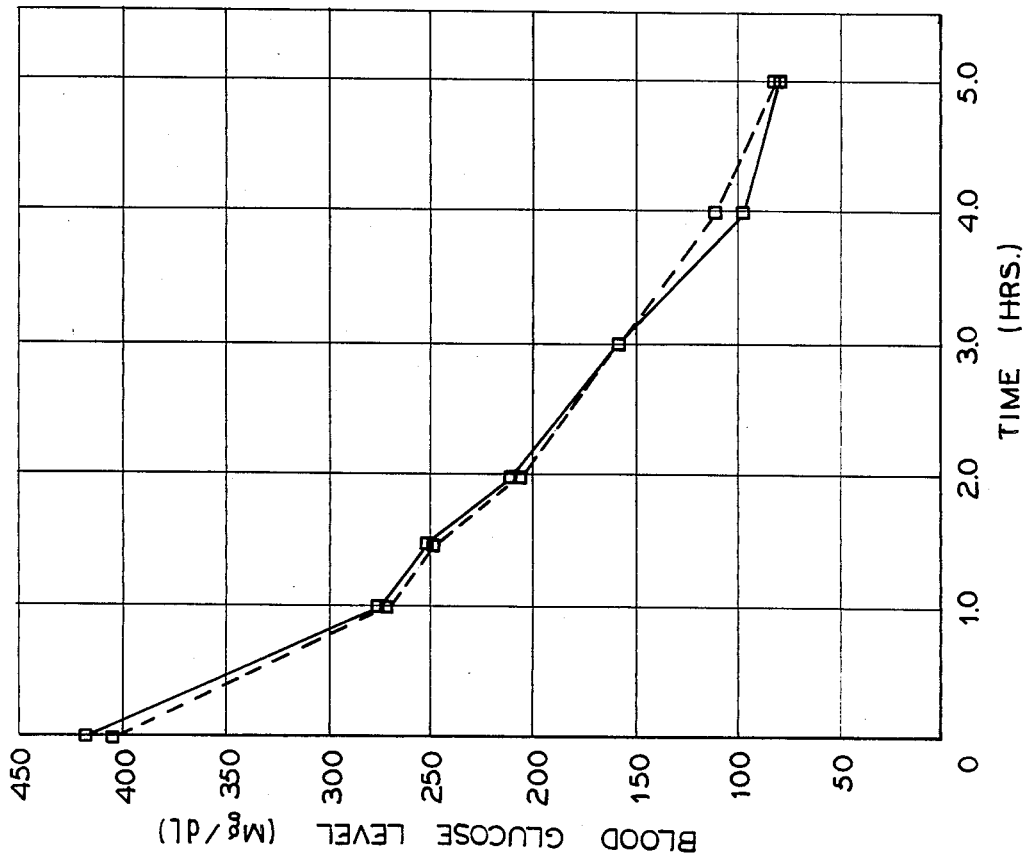
FIG. 18 illustrates the effect of Example 6 on blood glucose levels.

In FIG. 12, a 47 year old NIDDM female was given 6 capsules, 24 units of Example 6. In FIG. 13, a IDDM was given 14 capsules, 56 units, of Example 6. In FIG. 14, a IDDM was given 12 capsules, 48 units of Example 6. In FIG. 15, a 38 year old male IDDM was given 10 units of injectable insulin ([]), and on day 2, 10 capsules, 40 units of Example 6 (x). In FIG. 16, a 47 year old male IDDM, was given 10 units regular injected insulin ([]), and in day 2, 8 capsules (32 units) of Example 6 (x). In FIG. 17, a 49 year old male IDDM was given 10 units regular injected insulin ([]) and on day 2, 6 capsules (24 units) of Example 6 (x).

All subjects received two capsules of the lipolytic enzymes of Test 1-E with each dose of the composition of Example 6.

EXAMPLE 7

To produce the composition of Example 7, cholesterol (Fuluka, A. G.; Switzerland) and L-Arginine HCl (Wako Jun-Yaku, Japan; KWJ 3788) were mixed, at a two to one ratio, thoroughly in a vessel. Gum Acacia (Yakuri-Kagaku, Japan; A001=03) was used as a filler.

A Lipid (Cholesterol) and an Amino Acid (L-Arginine HCl) were bound with Hydroxypropylcellulose containing Insulin (Novo Monocomponent Porchin Crystalline Insulin). Citric Acid was used as an inhibitor of the insulin-inactivating enzymes and as a pH adjuster. Triethylamine HCl was used as an insulin-stabilizer as well as an anti-foaming agent.

The method of combining the insulin to the particles was the same as in Example 1 with the spray air-flow rate being set at 12 L/min and the spray air pressure of 2.5 Kg/M$^2$.

The Lipid and Amino acid particles bound with the crystalline Insulin, were coated with a water soluble membrane comprising hydroxypropylmethylecellulose (Shin-Etsu-Kagaku, Japan). The above Insulin-bound Lipid-Amino Acid particles coated with a water soluble membrane were coated with a lipid coating comprising Polyethylene Glycol Fatty Acid Esters, Yolk Lecithin containing 5% Phosphatic Acid, and Oleic Acid (Sigma Chem., St. Louis). Tromethamine was used as a vulcanizer.

The resulting composition was placed into a hard gel capsule and enteric coated as in Example 1.

The resultant 240 mg capsules each contained:

| | |
|---|---|
| Cholesterol | $-2.011 \times 10^{-4}$ M |
| Sodium Lauryl Sulfate | $-7.982 \times 10^{-5}$ M |
| Arginine HCl | $-2.575 \times 10^{-4}$ M |
| Triethylamine HCl | $-2.060 \times 10^{-6}$ M |
| Citric Acid | $-6.563 \times 10^{-3}$ M |
| Oleic Acid | $-1.901 \times 10^{-2}$ M |
| Tromethamine (Fuluka, Switzerland) | $-1.902 \times 10^{-2}$ M |
| Gum Acacia (Yakuri Kagaku, Japan) | $-2.147 \times 10^{-2}$ Gm |
| Hydroxypropylcellulose-L | $-0.733 \times 10^{-2}$ Gm |
| Hydroxypropylmethylecellulose | $-0.458 \times 10^{-2}$ Gm |

-continued

| | |
|---|---|
| Yolk Lecithine (5% Phosphatidic Acid) | $-0.299 \times 10^{-2}$ Gm |
| Insulin (Novo) | $-8$ units |
| Methyl Paraben | $-5.780 \times 10^{-5}$ M |
| Propyl Paraben | $-1.245 \times 10^{-5}$ M |
| Silica Gel | $-0.458 \times 10^{-2}$ GM |

The composition of Example 7 produces an activity similar to a subcutaneous injection of Regular Insulin in Men.

It is believed that the following ranges can be utilized for a composition made in accordance with Example 7. Each resultant 240 mg capsule may consist of:

| | |
|---|---|
| Cholesterol | $-(1.609$ to $2.413) \times 10^{-4}$ M |
| Sodium Lauryl Sulfate | $-(5.587$ to $9.978) \times 10^{-5}$ M |
| Arginine HCL | $-(1.931$ to $3.219) \times 10^{-4}$ M |
| Triethylamine HCL | $-(1.545$ to $2.575) \times 10^{-6}$ M |
| Citric Acid | $-(4.266$ to $8.860) \times 10^{-3}$ M |
| Oleic Acid | $-(1.426$ to $2.376) \times 10^{-4}$ M |
| Troethamine | $-(1.331$ to $2.568) \times 10^{-2}$ M |
| Gum Acacia | $-(1.825$ to $2.576) \times 10^{-2}$ Gm |
| Hydroxypropylcellulose-L | $-(0.115$ to $0.298) \times 10^{-2}$ Gm |
| Hydroxypropylmethylcellulose | $-(0.275$ to $0.641) \times 10^{-2}$ Gm |
| Yolk Lecithin (5% Phosphatidic Acid) | $-(0.115$ to $0.298) \times 10^{-2}$ Gm |

The final, coated oral insulin powders may be placed into a hard gel capsule, soft gel capsule, or into a hard-pressed table forms. These forms may be enteric coated.

EXAMPLE 8

A composition was made pursuant to the formulation of Example 7, however, the resultant formulation was modified as follows:

Each 240 mg of above containing Capsule, may consist of:

| | |
|---|---|
| Cholesterol | $-2.413 \times 10^{-4}$ M |
| Sodium Lauryl Sulfate | $-8.081 \times 10^{-5}$ M |
| Arginine HCL | $-2.592 \times 10^{-4}$ M |
| Triethylamine HCL | $-2.073 \times 10^{-6}$ M |
| Citric Acid | $-3.024 \times 10^{-3}$ M |
| Oleic Acid | $-2.376 \times 10^{-4}$ M |
| Troethamine | $-8.764 \times 10^{-6}$ M |
| Gum Acacia | $-2.119 \times 10^{-2}$ Gm |
| Hydroxypropylcellulose-L | $-0.737 \times 10^{-2}$ Gm |
| Hydroxypropylmethylcellulose | $-0.461 \times 10^{-2}$ Gm |
| Yolk Lecithin (5% Phosphatidic Acid) | $-0.115 \times 10^{-2}$ Gm |
| Insulin (Novo) | $-8$ units |
| Methyl Paraben | $-5.815 \times 10^{-5}$ M |
| Propyl Paraben | $-1.153 \times 10^{-5}$ M |
| Silica Gel | $-0.461 \times 10^{-2}$ GM |

TEST 8

Seven Insulin-Dependent Diabetics (IDDM) patients, 6 males and one female, between 24 to 47 years old (average 34.4) weighing between 48 and 68 Kg each (average 58.6 kg) took between 32 to 48 (average 42.6) International Units of Oral Insulin Formulation of Example 7, orally, after fasting overnight and fasting throughout the study.

Figure 22:
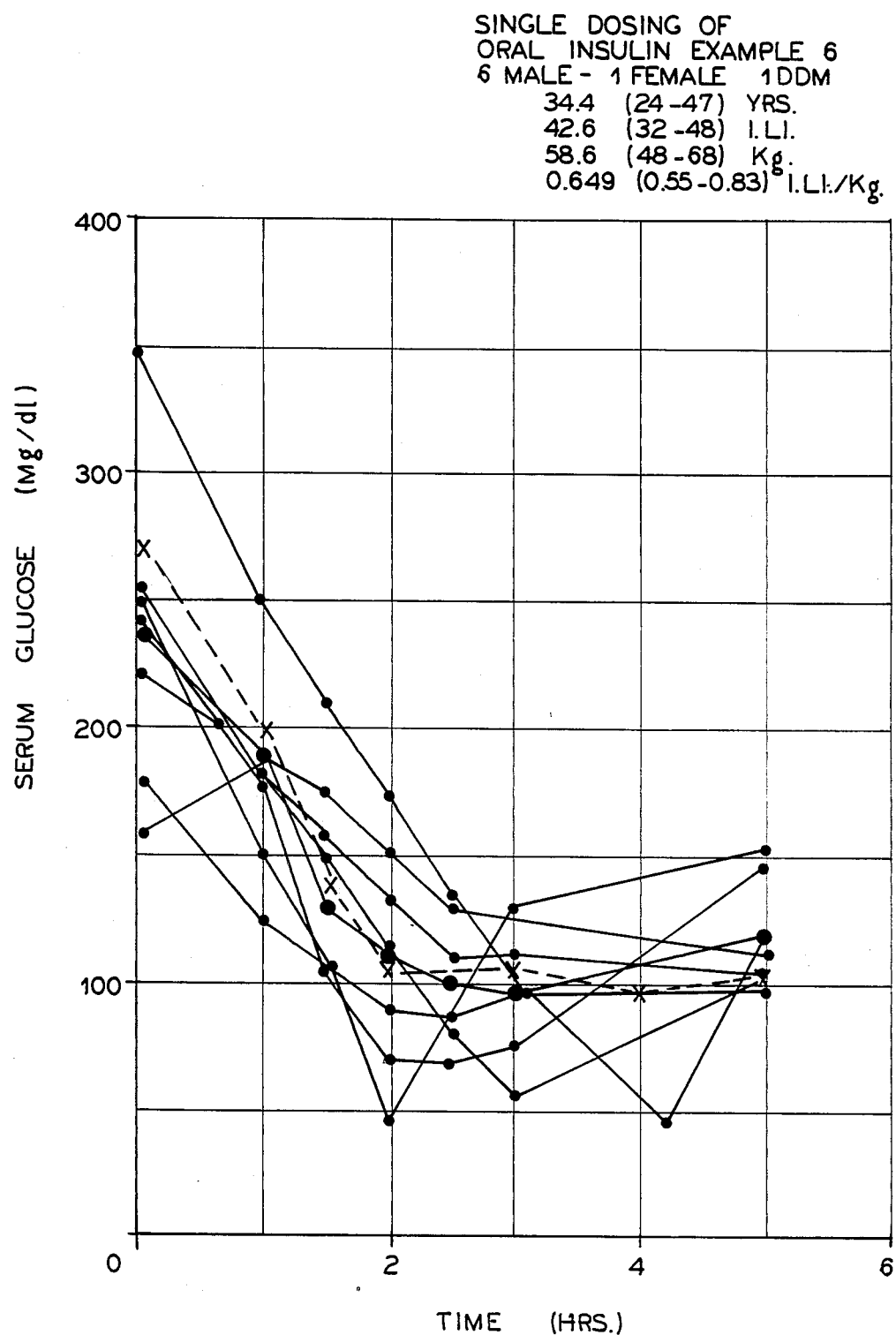
FIG. 22 is a comparison of the oral insulin of Example 7 versus regular injectable insulin.

5 male IDDM patients were given 0.172 IU/Kg of Regular Injectable Insulin (Tong-Shin) subcutaneously after fasting overnight and throughout the study in another 5 male IDDM patients, the overall effect of Oral Insulin Formulation of Example 7 in reducing serum glucose levels is similar to that of regular injectable insulin (see FIG. 22).

| PREPARATION | DOSE (iu/kg) | SERUM GLUCOSE (Mg/dl) | | | | |
|---|---|---|---|---|---|---|
| | | 00 | $C_{min}$ | $T_{C\text{-}min}$ | $T_{100}$ | dC/dT |
| Regular Insulin | 0.172 | 271 | 94.5 | 4.0 | 2.1 | 59.16 |
| Oral Insulin Form 0914 | 0.649 | 237 | 98.9 | 3.0 | 2.5 | 59.08 |

$C0$ = Base Value of Glucose;
$C_{min}$ = Minimum Value of Glucose Observed;
$T_{c\text{-}min}$ = Time of observing the minimum glucose level;
$T_{100}$ = Time to reach 100 mg/dl;
dC/dT = The Rate of Hypoglycemic Action.

In two IDDM patients, bioavailability of insulin (insulin levels in serum) was measured after oral administration of Oral Insulin Formulation of Example 7 (0.63 I.U./Kg).

Compared to 0.172 IU/Kg of Regular Insulin, subcutaneous injection in 5 IDDM patients, the 'pharmacokinetic and bioavailability' of insulin are as follows:

| PREPA-RATION | DOSE OF INSULIN | SERUM INSULIN (micro-U/ml) | | | | | |
|---|---|---|---|---|---|---|---|
| | | $I_O$ | $I_{max}$ | $T_{I\text{-}max}$ | $T_{I\text{-}O}$ | dI/dt | AUC |
| Reg. Insulin | 0.172 | 8.0 | 20.3 | 1.5 | 4.8 | 38.29 | 305.3 |
| Oral Insulin Form 0914 | 0.630 | 14.0 | 136.4 | 2.5 | 5.5 | 86.22 | 1,426.8 |

$I_O$ = Base Value of Insulin;
$I_{max}$ = Maximum value of serum insulin;
$T_{I\text{-}max}$ = Time of observing the maximum value of serum insulin;
$T_{I\text{-}O}$ = Time to reach the base value of serum Insulin;
dI/dT = the rate of rise of serum insulin (absorption rate);
AUC = area under the curve of serum insulin levels over the study period-time.

Each subject in Test 8 was given two capsules of the lipolytic enzyme composition set forth in Test 1-E with each dose of oral insulin.

The clinical study demonstrated that the Oral Insulin Formulation of Example 7 at an oral single dosing of 0.630 I.U./Kg of insulin caused an identical "hypoglycemic" (or effect in reducing serum glucose) effect in diabetics as that of after subcutaneous injections of 0.172 IU/Kg of insulin Regular Injectable Insulin (Tong-Shin) in another group of Insulin-Dependent Diabetics. Four and our 7 studied Insulin-Dependent Diabetics experienced an insulin-shock, corrected by oral ingestions of sugar water and fresh orange juice.

However, the pharmacokinetic and bioavailability date after 0.630 IU/Kg of Oral Insulin Formulation of Example 7, compared to that of 0.172 IU/Kg subcutaneous injection of Regular Injectable insulin (Tong-Shin), indicated that the rate of insulin absorption was more than twice as rapid after Oral Insulin than after injection of Regular Insulin. The bioavailability of insulin (AUC) after Oral Insulin (0.630 IU/Kg) is almost 4.7 times of AUC after subcutaneous injection of Regular Insulin (0.172 IU/Kg). The AUC after adjusting the administered insulin dosage after Oral Insulin is 2,264.8/IU and it is 1,775.0/IU after subcutaneous injection of Regular Insulin. The bioavailability of Oral Insulin Formulation of Example 7 is equal to or larger than that of Regular Injectable Insulin, per give insulin dosage.

The effect of Oral Insulin Formulation of Example 7 in reducing serum glucose in diabetics and the bioavailability of insulin in diabetics after oral administration of Oral Insulin Formulation of Example 7 are excellent and are similar to that of subcutaneously injected Regular Injectable Insulin in Insulin-Dependent Diabetics.

EXAMPLE 9

In this example, the lipolytic enzymes are lipid and enteric coated and can be combined with an oral insulin formulation into a single capsule or tablet.

A. PANCREATIC LIPASE

Pancreatic lipase particles were prepared as follows. The following components were placed in the modified Spir-A-Flow previously described.

| Materials | Quantity | Maker/Lot # (if applicable) |
|---|---|---|
| Pancreatic Lipase | 700 Gms | Sigma, St. Louis: No-L-3126 (Lot No. 74F-0470) |
| Corn Starch | 148.7 Gms | Shinwa Yakuhin, Japan (S 8285) |
| Methyl Paraben | 12.0 Gms | Sigma (32F-0511) |
| Propyl Paraben | 1.5 Gms | June-Sei, Japan (9L1202) |

The components were placed on the disk of the Spir-A-Flow and dried at a temperature ranging between approximately 30° and 32° C. while the rotor was rotated at 300 rotations-per-minute (rpm), the agitator at 500 rmp, and the chopper at 2,000 rpm. Fine dried particles of the components were thereby created that were blown from the bottom of the base by air heated to a temperature of approximately 30° to 32° C. The heated air was blown through the slit created between the rotor and the wall of vessel (slit air) and through the fine mesh-openings on the rotor disk (fluid air). Both the slit air and fluid air were at an air-pressure ranging between 100 and 450 mmH$_2$O. The fine particles of the components were suspended within the vessel of the Spir-A-Flow by the slit air and the fluid air. The particles of the components were then coated with the following coating solution:

| Chemicals | Quantity | Maker/Lot # (if applicable) |
|---|---|---|
| Hydroxy-propyl-Methylcellulose-L (HPMC-L) | 12.5 Gms | Shinwa Yakuhin, Japan (191184) |
| Sodium Lauryl Sulfate | 360.5 Mgs | Yakuri Kagaku, Japan (S316-06) |
| Water | | Added to chemicals until total solution was 250 ml |

To coat the particles with the coating solution, the coating solution was sprayed onto the particles of the components as they were suspended within the vessel, at a rate of 10 ml/min and at a pressure of between 1.0 to 5.0 Kg/M$^2$ for 120 minutes (the spray nozzle was 'on' for 20 to 40 seconds, and 'off' for 60 to 90 seconds, intermittently).

This resulted in the pancreatic lipase particles being coated, and thereby shielded, by a thin layer of HPMC-L membrane, which is water soluble. These particles of pancreatic lipase, coated with a HPMC-L membrane, were then enteric coated using the following entering coating solution:

| Chemicals | Quantity | Maker/Lot # (if applicable) |
|---|---|---|
| Hydroxy-proply-Methylcellulose-L | 4.5% | Shinwa Yakuhin, Japan (191184) |
| Polyethyleneglycol-6000 | 0.5% | Kao Sekken, Japan |
| Dichloromethane | 47.3% | |
| Ethanol | 37.8% | |
| Water | 9.4% | |

The above enteric coating solution had a pH of approximately 5.2 to about 5.6.

Alternatively, a commercial grade of acrylic resin called EUDRAGIT® L-100-55 (or L-100) or EUDRAGIT®-L30-D-55 can be utilized to coat the particles.

| Chemicals | Quantity | Maker/Lot No.(if applicable) |
|---|---|---|
| EUDRAGIT® L-100-55 | 12.5% solution, 480 parts by weight | Rohm Pharma, Weiterstadt, W. Germany |
| Ethanol or Isopropyl alcohol | 502 parts | |
| Polyethyleneglycol-6000 | 6 parts | Kao Sekken, Japan |
| Magnesium Stearate | 12 parts | |
| | 1,000 parts | |
| Or, EUDRAGIT®-L30-D55 | 30% solution, 1,000 parts by weight | Rohm Pharma, Weiterstadt, W. Germany |
| Polyethyleneglycol-6000 | 30 parts | Kao Sekken, Japan |
| Water | 898 parts | |
| Silicone emulsion | 2 parts | |
| Talc | 70 parts | |
| | 1,000 parts | |

The particles were enteric coated using the first mentioned enteric coating solution by spraying the enteric coating solution onto the HPMC-L coated particles of pancreatic lipase, as the particles were again suspended in the vessel, at a spraying rate of 10 ml/min and a pressure of 2.5 Kg/M$^2$ for three (3) to four (4) hours. The spraying nozzle was 'on' for 20 to 40 seconds and 'off' for 60 to 120 seconds. The resultant product provides the desired dissolution time in "gastric solution" and in "duodenal solution."

B. BILE SALT

Bile salt particles were created by coating with a Spir-A-Flow bile salt and avicel with the coating solution and the first mentioned enteric coating solution used to coat the pancreatic lipase above. The bile sale and avicel were coated as set forth in A above. The bile salt and avicel components used were as follows:

| Materials | Quantity | Maker/Lot # (if applicable) |
|---|---|---|
| Bile Salt | 406.6 Gms | Dilco (714720) |
| Avicel | 69.1 Gms | Shinwa Yakuhin, Japan |

C. ORAL INSULIN FORMULATION

The oral insulin formulation was created as follows. The following components were mixed in the Spir-A-Flow.

| Components | Quantity | Makers/Lot No. (if applicable) |
|---|---|---|
| Cholesterol | 220.5 Gms | Kaksan, Kagaku Japan(D850134) |
| Arginine HCl | 110.2 Gms | Furuka, Switzerland |
| Gum Acacia | 24.0 Gms | |

-continued

| Components | Quantity | Makers/Lot No. (if applicable) |
|---|---|---|
| Glycine | 31.2 Gms | |
| Sodium Lauryl Sufate | 48.0 Gms | |
| Propyl Paraben | 3.3 Gms | June-Sei, Japan (9L1202) |

The components were thoroughly mixed and dried in the vessel of the Spir-A-Flow. The following parameters were utilized in the Spir-A-Flow: the rotor was set at 350 rpm; the agitator was set at 500; the chopper was set at 2,000 rpm; the slit air pressure was between 100 to 300 mmH$_2$O; the fluid air pressure was between 100 to 350 mmH$_2$O; the air was at a product temperature of 24° to about 31°,C.; the components were mixed and dried in the Spir-A-Flow at these parameters for approximately 30 minutes. Then, thoroughly mixed and dried components, that are suspended in the air of the vessel, were bound with the following binding solution.

| Chemicals | Quantity | Maker/Lot No. (if applicable) |
|---|---|---|
| Hydroxy-propyl-Cellulose-L (HPC-1.) | 16.0 Gms | Shinwa Yakuhin, Japan (191184) |
| Sodium Lauryl Sulfate | 1.0815 Gms | Yakuri-Kagaku, Japan (S316-06) |
| Trimethylamine | 0.8150 Gms | Wako Kagaku, Japan |
| Citric Acid | 1.2608 Gms | Yakuri-Kagaku, Japan (KA9105) |
| Crystalline Insulin | As desired in grams | (SIGMA Bovine Insulin crystalline) |
| Water | 220 ml | the pH of the solution was approximately 2.0 to about 3.5 |

To coat the particles created above, the binding solution was sprayed through the spray nozzle that is located at the top of the Spir-A-Flow, see 28 of FIG. 3, the binding solution was placed in a cylinder and then was cooled by being submerged in an ice cold beaker, before and during the spraying process. The binding solution was coated onto the fine air suspended particles, at a rate of 10 to 14 ml/min, at an air pressure of 1.0 to 2.0 Kg/M$^2$ and an air volume of 15 to 25 L/min, for approximately two hours; until all the binding solution is used. The spray nozzle was turned 'on' for 20 to 40 seconds, and 'off' for 30 to 90 seconds, intermittently. Throughout the process, the product temperature was kept at between approximately 25° to about 32° C. by maintaining the air used to suspend the particles at this temperature. The resultant particles having the crystalline insulin were then immediately dissolved in water, having a temperature of approximately 24° C., creating an emulsion having the fine particle bound insulin. The emulsion has a pH of approximately 4.2 to about 5.4.

Immediately, thereafter, the insulin-bound particles contained in the emulsion were then coated with a lipid coating solution created as follows. The following components comprise the lipid coating that was sprayed on to the insulin bound particles.

| Chemicals | Quantity | Maker/Lot No.(if applicable) |
|---|---|---|
| Yolk lecithin | 24.0 Gms | Sigma, St. Louis |
| Polyethylene-glycol-Fatty acid ester | 18.7 Gms | Kao Sek-ken, Japan (Emanon 3199; Lot No. 12744Y) |
| Water | | added to a final volume of 200 ml. The resultant solution had a pH of approximately 5.5 to about 6.5 |

The lipid coating solution was also sprayed through the spray nozzle 28 located at the top of the vessel. The parameters of the Spir-A-Flow were as follows: the rotor was set at 250 to 300 rmp; the agitator at 500; and the chopper at 2,500 to 3,000 rpm. The spray nozzle and its spraying rate was set at 12.0 ml/min at an air pressure of 1.2 to 1.5 Kg/M$^2$, an air volume of 15 to 20 L/min, and the product temperature was between approximately 30° to about 34° C. Again, the product temperature is maintained by setting the thermal regulator of the Spir-A-Flow so that the air that flows into the vessel has the desired temperature. The lipid coating solution was sprayed for 60 minutes. The spraying nozzle is turned 'on' for 20 seconds and 'off' for between 60 to 90 seconds, intermittently.

The resultant lipid coated particles are then re-coated with a recoating lipid coating solution. The recoating lipid coating solution contains the following components.

| Chemicals | Quantity | Maker/Lot No. (if applicable) |
|---|---|---|
| Oleic acid | 7.5 Gms | Junsei-Japan |
| Cholesterol | 3.0 Gms | Furuka, A.G. (246537-784) |
| Trometamol | 2.5 Gms | Pharmacia, Sweden |
| Alcohol | to 100 ml. | (warmed to 80–90° C. before mixing the other components) |

The recoating lipid solution was sprayed from the side of the Spir-A-Flow vessel at a spraying rate of 12 ml/min, at an air pressure of 1.0 to 1.5 Kg/M$^2$, and at an air volume of 15 to 20 l/min. The rotor was set at 300 to 350 rpm, the agitator at 500, the chopper at 3,000 to 3,500 rpm, and the temperature of the product was maintained at approximately 31° to about 35° C. The spray nozzle was turned on for 20 to 40 seconds, and was turned 'off' for 60 to 90 seconds, intermittently.

If desired, trometamol can be omitted from the recoating lipid solution. However, if trometamol is omitted it will result in an increased drying time and extreme care will have to be taken to prevent an 'overly greasy, wetness' of the particles. Tromethamine (trometamol) is listed on U.S. and European Pharmacopea.

After the recoating lipid solution step, the coated dried particles are either placed into hard-gel capsules or compressed into a tablets form. The oral insulin bound coated particles can be made into capsules or tablets alone or can be mixed with the enteric coated particles of lipase and bile salt previously described. The resultant capsules or tablets can be enteric coated.

Alternatively, the lipid-coated bound oral insulin particles may themselves be enteric coated. The enteric coating solution for coating the lipid coating oral insulin particles includes the following components:

| Chemicals | Quantity | Maker/Lot No. (if applicable) |
|---|---|---|
| EUDRAGIT ® L 30D | 1,000 parts (30% solution) | Rohm Pharma GmbH, West Germany |
| Polyethylene-glycol-6000 | 30 parts | |
| Talc (powder) | 70 parts | |
| Silicone emulsions | 2 parts | |
| Water | 898 parts | |
| | The resultant solution has a pH of approximately 5.5 to about 6.5 | |

To create enteric coated, lipid coated oral insulin particles, the enteric coating solution was sprayed through the spray nozzle 28 that is located in top of the vessel of the Spir-A-Flow at a spray rate of one gram per Kg per minute for approximately 500 grams of the lipid coated bound oral insulin particles. The particles were sprayed for 5 seconds and allowed to dry for 5 seconds, intermittently, until the desired thickness of the enteric coating was achieved.

To determine the amount of enteric coating solution to be applied in percent dry lacquer substance (enteric coating solution) ("Q") the surface area of the particle to be coated (SA) in $mm^2$ is multiplied by the mg of dry lacquer (L) per $Cm^2$ desired in $mg/Cm^2$ (thickness of the coating), this is divided by the weight of oral insulin bound particle (W) in mg. Accordingly, the percent dry lacquer substance "Q" is calculated by the following equation:

$$Q=(SA\times L)/W$$

Preferably, the enteric coated particles of the oral insulin have a diameter of between approximately 0.1 to about 0.8 mm (the surface areas thus ranging between approximately 0.314 to about 2.0 $mm^2$). It has been found that by spraying approximately 120 to about 150 ml of the above enteric coating solution onto oral insulin particles weighing approximately 450 gms, the resultant coated particles will not dissolve when placed in a solution having a pH of approximately 1.2 (a gastric solution) for at least 10 minutes; however, the coated particles will dissolve and disperse in a solution having a pH of approximately 6.8 (a duodenal solution) within 30 seconds. Accordingly, an ideal enteric coating for the oral insulin particles is achieved.

D. ORAL INSULIN PARTICLE/LIPASE/BILE SALT CAPSULE

In this example, capsules including the oral insulin coated particles, coated lipase and coated bile salt are created. To this end, to each #1-sized hard-gel capsule, the enteric coated oral insulin particles (prepared as described above in C), enteric coated lipase particles (prepared as described above in (A), and enteric coating bile salt particles (prepared as described above in (B) are mixed together and placed in hard-gel capsules in the following ratio:

200 Mg (12 IUS) of Oral Insulin
28 Mg (1,000) Units of Pancreatic Lipase
25 Mg of Bile Salt
50 Mg of Sodium Bicarbonate (oven-dried); and
50 Mg of Citric Acid as "filler."

The sodium bicarbonate and citric acid affords a bursting effect causing the hard-gel capsules to open in the stomach, releasing the enteric coated particles of oral insulin, lipase, and bile salt in sizes less than 1 mm. Due to their size and composition, these particles are rapidly passed through the pylorus into the duodenum. The sodium bicarbonate and citric acid also function to adjust the intra-intestinal pH toward alkalinity and increases the activities of the pancreatic lipase in the presence of the bile salt.

E. COMPARATIVE CLINICAL STUDY OF THE ORAL INSULIN FORMULATION OF C vs. THE ORAL INSULIN FORMULATION OF D

Six diabetics (3 Insulin-dependent and 3 Non-insulin-dependent; five males and one female) participated in a comparative study between the oral insulin formulation of C given together with four capsules of lipolytic enzyme, each containing 1000 units of lipase and 25 Mg of bile salt, and the oral insulin formulation of D, i.e. the oral insulin formulation of C combined with the coated lipase of A, coated bile salt of B, sodium bicarbonate, and citric acid in a hard-gel capsule.

Each patient received, on separate days, each formulation. To this end, each patient orally received 48 IU of Oral Insulin with four capsules containing 4,000 Units of lipase and 100 mgs of bile salt on the first day of study, and 4 capsules containing 48 IU of oral insulin and 4,000 Units of lipase and 100 mgs of bile salt on the second day of the study. On the third and fourth day of the study, the routine was repeated.

In general, whether the lipolytic enzyme capsules were given separately but concomitantly with the oral insulin (48 IU) capsules or the lipolytic enzymes were contained in same capsule with the oral insulin and given as a combined capsule, the overall effect on blood sugar and hypoglycemic action/effect of the oral insulin was the same.

F. ORAL INSULIN/LIPASE/BILE SALT TABLET

The nonenteric coated particles described in the Section A, B, and C can be combined and made into a hard-pressed tablet form. To this end, the following components were mixed.

| | |
|---|---|
| Insulin/Lipase/Bile Salt Particle (in the same proportion as set forth in D above) | 126.35 Gm |
| Sodium Bicarbonate | 50.0 Gm |
| Potassium Bicarbonate | 32.0 Gm |
| Citric Acid | 17.65 Gm |
| Talc | 500 Mg |
| Avicel | 500 Mg |
| Lactose | 45.0 Gm |
| Corn Starch | 28.0 Gm |
| | 300.00 Gm |

The above mixture was made into approximately 220 mg-size (if desired the size can be more or less), hard pressed tablets. If crystalline insulin is substituted in the formulation of Section C, each tablet can contain 6 IU of insulin; the insulin dose can be increased up to 40 IU, if desired.

The resultant tablets were coated with EUDRAGIT®-E-100 at a final "film-coating" thickness of approximately 0.1 to about 0.15 mm. Tablets so coated were found to dissolve in Gastric juice Solution having a pH of up to 5.0, within 30 seconds or less. The particles thereby released, i.e., oral insulin, lipase, and bile salt, because they have been enteric coated, only readily dissolve in a solution having a pH of 6.0 or more. Moreover, the particles will have a size of less than 1 mm and therefore will readily pass through the pylorus and dissolve in the duodenum. In the duodenum the particles are emulsified and suspend the micro-lipospheric particles having insulin bound thereto (having a size of less than 1 micron) and/or "lipid-layer coated"—micro-lipospheric-bound insulin (have a size of less than 50 microns in size). Accordingly, the particles will be suspended in an emulsion formed within the lumen of duodenum. These particles are thereby preferably absorbed from the villae on the intestinal mucosa, bypassing the liver.

Clinical studies of the tablet form of the oral insulin/-lipase/bile salt were conducted in three insulin-dependent diabetics and the results were as follows:

| Name | Sex | Wt | Age | Diabetes | Dose | Blood Sugar (Mg %) | | | | | |
|---|---|---|---|---|---|---|---|---|---|---|---|
| | | | | | | 0 | 1 | 2 | 3 | 4 | 5 |
| JSL | M | 59 | 56 | IDDM | 60 IU | 168 | 142 | 126 | 115 | 103 | 88 |
| KCK | M | 55 | 63 | IDDM | 60 IU | 195 | 175 | 157 | 135 | 108 | 62 |
| KSK | M | 58 | 42 | IDDM | 48 IU | 152 | 132 | 120 | 99 | 72 | |

The use of an enteric coating solution such as Eudragit®-L 100 or L-30 to coat the oral insulin particles, bile salt particles, and lipase particles provides the coated particles with the following characteristics:
1. resistance to gastric juices;
2. protects the stomach lining against any corrosives provided by the particles.
3. isolates the incompatible drugs;
4. improves the shelf life of the products;
5. insulates the hygroscopic cores; and
6. protects the particles against atmospheric influences.

As set forth above, the Eudragit® protects the stomach wall from any corrosive effect the bile salt may have and also improves the oral insulin formulas that have a poor shelf life and are extremely labile and hygroscopic.

EXAMPLE 10

Pursuant to this example, an oral insulin formulation was prepared. The following components were placed into the vessel of the Spir-A-Flow.

| Components | Quantity | Maker/Lot No. (if applicable) |
|---|---|---|
| Cholesterol | 250–350 Gms | Koksan Kagaku, Japan (D850134) |
| Arginine HCl | 120–180 Gms | Junsei Chem. Co., Japan (1A1527) |
| Aminoacetic Acid | 30–50 Gms | Yakuri Kagaku, Japan (171092) |
| Sodium Lauryl Sulfate | 30–60 Gms | Yakuri Kagaku, Japan (S316=05) |
| Propyl Paraben | 5–10 Gms | Junsei Chem. Co., Japan (9L1202) |

These powdery components were ground by using the Jet Mill previously described (see FIGS. 1 and 2) into particle sizes of less than 50 microns, and thoroughly mixed and dried in the vessel of the Spir-A-Flow utilizing the following parameters:

| | |
|---|---|
| Rotor (rotation per minute) | = 250–300 Fluid Air Pressure = 40–50 mmH$_2$O |
| Agitator (rpm) | = 500–700 Slit Air Pressure = 25–35 mmH$_2$O |
| Chopper (rpm) | = 4,000–5,000 Supply (Main) Air Pressure = 900–1,000 mmHg |

The thoroughly mixed and dried components (particles) were then suspended in the vessel by increasing the slit air pressure and the fluid air pressure to approximately 50 to about 100 mmH$_2$O. The suspended, fine, dried particles were then coated with the following solution:

| Components | Quantity | Maker/Lot No. (if applicable) |
|---|---|---|
| Hydroxy-Propyl-Methylcellulose-L | 15–25 Gms | Shinwa Yakuhin, Japan (191184) |
| Triethylamine | 0.5–1.0 Gms | Wako Kagaku, Japan |
| Citric Acid | 0.05–0.10 M | Yakuri Kagaku, Japan (KA9105) |
| Sodium Lauryl Sulfate | 1.00–1.500 Gms | Yakuri Kagaku, Japan (S316=05) |
| Insulin crystalline | as desired from 8–20 IUS | Eli Lilly (Bovine Insulin) |
| Water | To a final volume of 400 ml, at a temperature of approximately 10 to about 12° C.; and a final pH of approximately 1.2 to about 2.5 | |

The binding solution is sprayed from the spray nozzle located at the top of the vessel so that it coats the particles. The binding solution containing the insulin crystalline is bound to the fine, dried particles utilizing the following parameters:
Rotor=200–300 rpm
Spray Pump Flow Rate=12.0–15.0 ml/min
Agitator=500–700 rpm
Spray Air Pressure=1.2–1.5 kg/Cm$^2$
Chopper=2,800–3,500 rpm
Spray Air Volume=20–40 L-Min
Fluid Air Pressure=50 to 80 mmH$_2$O
Slit Air Pressure=50–90 mmH$_2$O
Main Supply Air Pressure=800–1,500 mmHg
Product Temp.=26.7°–28.5° C.

The particles were sprayed intermittently during an approximately 90 to about 120 minute period, until the entire bulk solution had been used. The particles were sprayed for approximately five seconds and dried for approximately 22 seconds during the period intermittently.

The particles bound with the insulin crystalline solution (bound particles) were then coated with a first coating solution. The first coating solution included the following:

| | | |
|---|---|---|
| Egg Yolk Lecithin | 15–24.0 Gms | Sigma Chemical |
| Polyethylene-glycol-Fatty Acid Ester (Emanon) | 12–16.0 Gms | Kao Sekken, Japan (Emanon 3199; 12744Y) |
| Polysorbate-80 | 1–5.0 Gms | Hayashi Pure Chemical, Osaka, Japan (Tween-80 IFM09818) |
| Water | To a final volume of 500 ml; Temp. of 25 to 26° C.; and pH of 4.5 to 6.5 | |

The above bound particles were then suspended in the Spir-A-Flow and were coated with the above first coating solution under the following conditions:
Rotor=220 to 300 rpm
Spray Pump Flow Rate=12.0–15.0 ml/min
Agitator=500–800 rpm
Spray Air Pressure=1.2–2.0 Kg/Cm$^2$
Chopper=2,800–4,000 rpm
Spray Air Volume=20–40 L/Min
Fluid Air Pressure=50–100 mmH$_2$O
Slit Air Pressure=50–100 mmH$_2$O
Main Supply Air Pressure=900–1,000 mmHg
Product Temp.=32.0°–33.8° C.

The bound particles were sprayed for approximately 5 to about 10 seconds, and dried for approximately 20 to about 22 seconds.

The coated bound particles were then re-coated with a second coating solution. The second coating solution contained the following:

| Chemicals | Quantity | Maker/Lot No. (if applicable) |
|---|---|---|
| Oleic Acid | 10–15.0 Gms | Junsei Chemical, Japan (9D4034) |
| Polysorbate-80 | 4–6.0 Gms | Hayashi Pure Chemical, Japan (IFM09818) |
| Ethanol | To final volume of 500 ml; Temp. 28–30° C,; pH 6.0 to 7.2 | |

The second coating solution was sprayed onto the suspended coated bound particles from the Spray Nozzle located on the side of the vessel utilizing the following parameters:
Rotor = 250–300 rpm
Spray Pump Flow Rate = 12.0–15.0 ml/Min
Agitator = 500–700 rpm
Spray Air Pressure = 1.2–15 Kg/Cm$^2$
Chopper = 3,000–4,500 rpm
Spray Air Volume = 20–40 L/Min
Fluid Air Pressure = 60–110 mm$H_2O$
Slit Air Pressure = 60–110 mm$H_2O$
Main Supply Air Pressure = 900–1,000 mmAg
Product Temp. = 30°–32.5° C.

The resultant coated bound particles, that include insulin and are coated with lipids, can either be made into fine granules having a size of less than 2 mm in diameter (using $NaHCO_3$:Citric Acid in a 3.1 ratio as a 'Seed' coated with a starch, that is coated with a coating layer, and insulin-bound chemical particles described above as the outer layer, etc., and then enteric coated), or mixed with Sodium Bicarbonate, 20 to 30% by weight; Citric Acid 10–20% by weight; and Silica Gel 3 to 6 grams per 500 to 650 grams of the final weight of the formulation, and placed into Number-4 sized hard-gel capsules. The resultant capsules were then enteric coated with the following enteric coating solution:

| Chemicals | Quantity | Maker/Lot No. (if applicable) |
|---|---|---|
| Hydroxy-Propyl-Methyl-Cellulose-Phthalate | 4.5% | Shinwa Yakuhin, Japan |
| Polyethyleneglycol-6000 | 0.5% | Kao Sekken, Japan |
| Dichloromethane | 47.3% | Yakuri Kagaku, Japan (224144) |
| Ethanol | 37.8% | |
| Water | 9.4% | pH = 5.2 to 5.6 |
| Shellac | 0.2 Gms per 100 ml of the above mixed solution is added to and dissolved (dark brown color) pH = 5.2 to 5.6; mixed at a temperature of approximately 30.0 to about 32.5° C. | |

Alternatively, an enteric coating solution containing the following components can be used:

| | | |
|---|---|---|
| EUDRAGIT ®-L30-D55 | 30% solution, 1,000 parts | Rohm Pharam, West Germany |
| Polyethyleneglycol-6000 | 30 parts by weight | Kao Sekken, Japan |
| Silicone Emulsion | 2 parts | |
| Talc | 70 parts | |
| Water | 898 parts | |

The first mentioned enteric coating solution was used to enteric coat the #4-capsule filled with the bound insulin particles. The bound insulin particles contained in the #4 capsules so coated were found to only dissolve in a gastric solution having a pH of approximately 1.2 after exposure for two or more hours. However, the capsules do dissolve in a duodenal solution having a pH of approximately 6.8 within fifteen (15) minutes or less, (as specified by the U.S. Pharmacopea). If capsules coated with the alternative enteric coating solution were also found to have similar characteristics.

EXAMPLE 11

To prepare the oral insulin formulation of this example, the following components were placed into the vessel of the Spir-A-Flow:

| Components | Quantity | Maker/Lot No. (if applicable) |
|---|---|---|
| Cholesterol | 350–500 Gms | Koksan Kagaku, Japan (D850134) |
| Sodium Lauryl Sulfate | 30–50 Gms | Yakuri Kagaku, Japan (S316-05) |
| Propyl Paraben | 5–10 Gms | Junesei Chemical, Japan (9L1202) |
| Methyl Paraben | 5–10 Gms | Junesei Chemical, Japan (OC1495) |

After the components were mixed and dried in the vessel of the Spir-A-Flow, utilizing the parameters described in Example 10 (above) these particles were bound with an insulin-containing binding solution. The insulin-containing binding solution contained the following:

| Chemicals | Quantity | Maker/Lot No. (if applicable) |
|---|---|---|
| Hydroxypropyl-methylcellulose-L | 15–25 Gms | Shinaw Yakuhin, Japan (191184) |
| Triethylamine | 0.5–1.0 Gms | Wako Kagaku, Japan |
| Citric Acid | 0.05–0.1 M | Yakuri Kagaku, Japan (KA9105) |
| Sodium Lauryl Sulfate | 1.00–1.500 Gms | Yakuri Kagaku, Japan (S316 = 05) |
| Silicone Emulsion | 0.3–1.0 Gms | |
| Insulin | (as needed to obtain a final capsule having 2 to 20 IU) | |
| Water | To a final volume of 400 ml, having a pH of approximately 1.2 to about 2.5 | |

The mixed and dried components were suspended in the vessel and the insulin-containing binding solution was sprayed from the spray nozzle 28 located at the top of the vessel. The binding solution was sprayed as the Spir-A-Flow operated at the conditions set forth in Example 10 above.

The insulin-bound particles are then coated with a first coating solution. The first coating solution contained the following chemicals:

| Chemicals | Quantity | Maker/Lot No. (if applicable) |
|---|---|---|
| Egg Yolk Lecithin | 15–24 Gms | Sigma Chemical |
| Emanon-3199 | 12–16 Gms | Kao Sekken, Japan (12744Y) |
| Tween-80 | 1–5 Gms | Hayashi Pure Chemical, Japan (IFM09818) |
| Water | To a final volume of 500 ml, having a pH of 4.0 to 6.2 | |

The coated insulin-bound particles were coated with the first coating solution as described in Example 10 (above).

The resultant coated particles were then re-coated with a second coating solution. The second coating solution had the following constituents:

| Chemicals | Quantity | Maker/Lot No. (if applicable) |
|---|---|---|
| Oleic Acid | 10–15.0 Gms | Junsei Chemical, Japan (9D4034) |
| Tween-80 | 4–6.0 Gms | Hayashi Pure Chemical, Japan (IFM09818) |
| Ethanol | To a final volume of 500 ml, having a pH of 6.0 to 7.2 | |

The second coating solution was sprayed from the spray nozzles 27 located on the side of the vessel under the conditions described in Example 10 (above).

The resultant coated particles can be made into fine granules having a size of less than 2 mm in diameter including sodium bicarbonate and citric acid, in a 3:1 or 1:1 ratio mixture, as the seed; starch as the nonpareil; coated with a coating layer; insulin-bound particles as the outer-layer; and enteric coated or mixed with approximately 20 to about 30% by weight of sodium bicarbonate, approximately 10 to about 20% by weight citric acid and approximately 0.5 to about 2.0% by weight of silica gel. The resultant mixtures can then be packed into Number-4 hard-gel capsules, and enteric coated.

EXAMPLE 12

Figure 23:
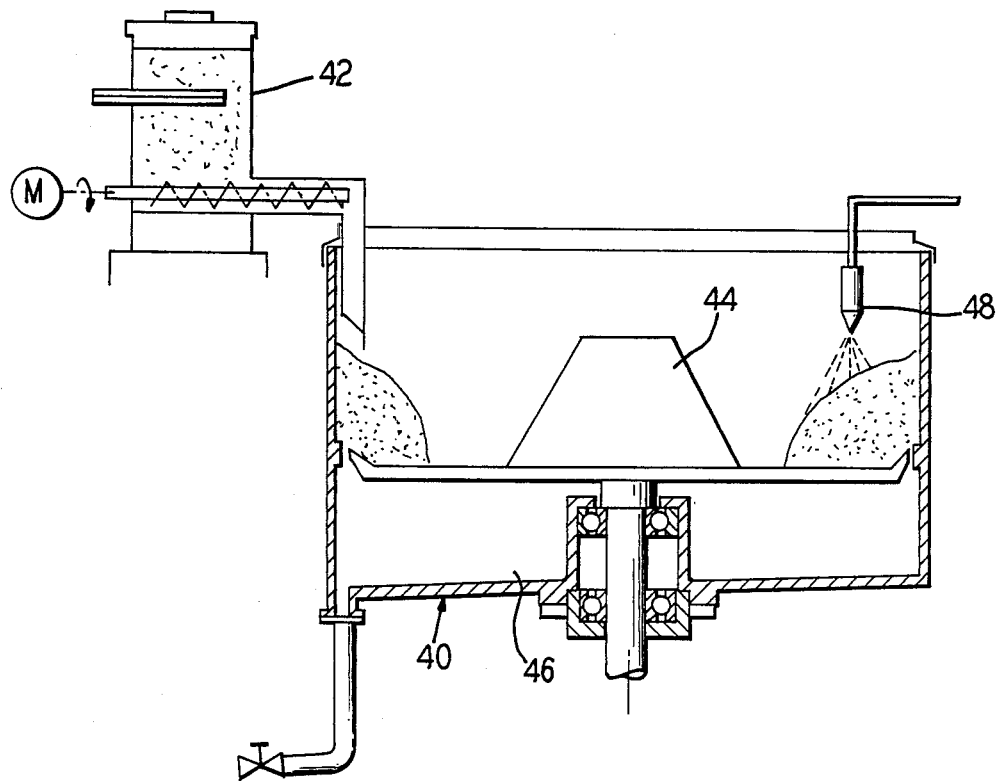
FIG. 23 illustrates a cross-sectional schematic of a CF granulator.

In this example, the oral insulin formulations made in Examples 10 and 11, comprised of granules having a diameter of less than 2.0 mm are coated. A CF Granulator (See FIG. 23) is utilized and the oral insulin formulation of either 10 or 11 was combined with sodium bicarbonate/citric acid in a ratio of approximately 3:1 having a size of less than 0.5 mm is applied as the "nonpareil." The resultant granules were then enteric coated with one of the previously described enteric coating solutions. It was found that the resultant granules would not dissolve for at least a two-hour period in a gastric solution having a pH of approximately 1.2 but will dissolve within 15 minutes or less in a duodenal solution having a pH of approximately 6.8. The CF Granulator, commercially available through Freund Industries, Inc., of Tokyo, Japan, has been designed to agglomerate, granulate and coat by applying a centrifugal system and is shown in FIG. 23. Briefly, the CF granulator 40 includes a power supply 42, rotor 44, air supply 46, and spray nozzle 48.

To create the product in the CF Granulator, the temperature of the air supply was set at between approximately 28° to about 34° C., the rotor speed was set at between approximately 130 to about 200 rotations-per-minute, the air supply flow rate was at 30 to 50 L/min, the spray nozzle's spray rate was at 20 to 50 ml/min at a Spray Pressure of 10 to 30 L/min.

To create the sodium bicarbonate/citric acid composition, citric acid, 110 to about 150 Gms, as a "seed", sodium bicarbonate powder, approximately 400 to about 450 Gms, and a small amount of alph-starch powder, approximately 10 to about 50 Gms, is over-coated over the citric acid, and dried for 30 minutes in Spir-A-Flow.

Using citric acid as the seed, and sodium bicarbonate and starch as the over-coat (both as the "nonpareil"), oral insulin formulations of examples 10 and 11 as powders premixed with approximately 30 percent by weight of starch, are coated onto a granular nonpareil by using approximately 6 to about 20 percent (preferably about 10%) of hydroxypropylcellulose-L (HPC-L) in alcohol at a rotor speed of approximately 100 to about 200 rpm, an air supply of 20 to 50 L/min, a spray nozzle flow rate of 15 to 40 ml/min at a pressure of 10 to 30 L/min for 20 to 40 minutes (the temperature was approximately 25° to about 30° C.). The resultant granules were dried in a Spir-A-Flow for 30 minutes at a temperature of approximately 30° to about 35° C.

Figure 24:
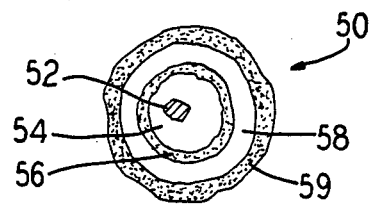
FIG. 24 is a schematic illustration of an oral insulin granule of Example 12.

The resultant granular formulation had granules having a diameter of between approximately 0.490 to about 1.450 mm and were enteric coated by using an enteric solution of 5% HPC-methyl-phthalate and polyethyleneglycol-6000 (0.5%) dissolved with ethanol. Other enteric coating solutions set forth above could also have been utilized. The granules were coated with the enteric solution at a rotor speed of approximately 150 to 250 rpm, air supply at 30 to 50 L/min, spray flow at 20 ml/min at pressure of 15 to 30 L/min, and at a temperature of approximately 25° to 30° C. The resultant granules have a structure substantially similar to that illustrated in FIG. 24. The granule 50 includes a core or seed 52, a nonpareil 54, a HPC-L coating 56, a layer of insulin 58, and an enteric coating 59. These granules would not dissolve for at least 2 hours in a gastric solution having a pH of approximately 1.2, but, would dissolve within 15 minutes or less in a duodenal solution having a pH of approximately 6.8.

TEST 12A

The resultant product, approximately 0.9 (0.69 to 1.07) IU per Kg, was dissolved in 10 to 20 ml of saline, in vitro, and administered into the duodenum of three dogs via a Wallace-Diamond double lumen tube. Serial femoral venous blood samples were collected at time 0, 60, 80, 100, 180, 240, and 300 minutes after the administration of formulation in 3 dogs. The dogs, one male and two female, had an average weight of 4.0 (approximately 3.0 to about 5.6) Kg each. Plasma glucose levels and insulin levels (by radioimmunoassay and Wako's enzymatic-immunoassay methods) were measured.

Figure 25:
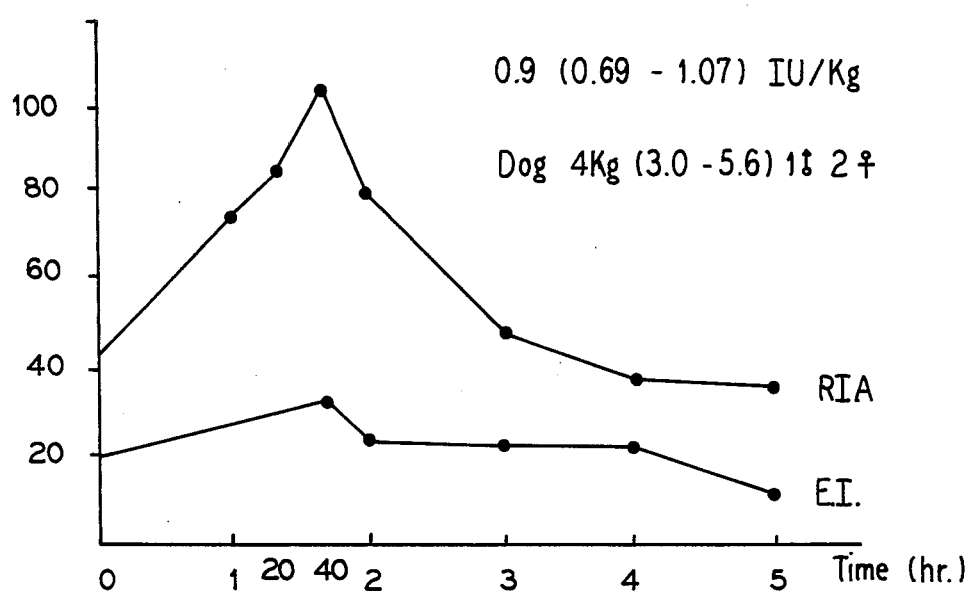
FIG. 25 illustrates the insulin levels in the blood of dogs given the insulin formulation of Example 12.
Figure 26:
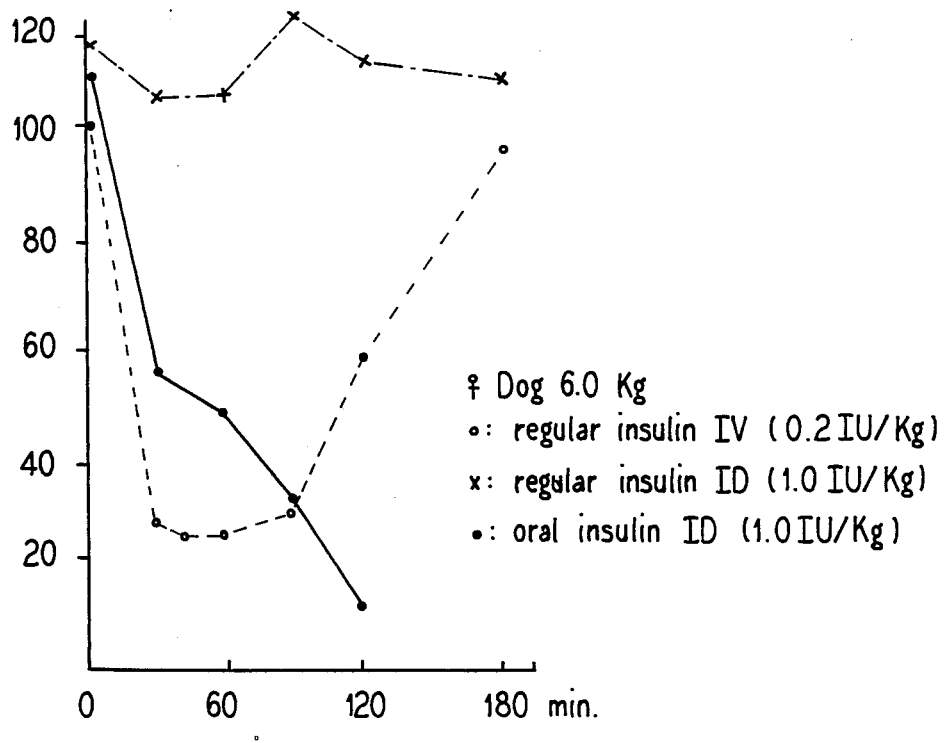
FIG. 26 illustrates the effect of the oral insulin granules of Example 12 on blood sugar levels of dogs.

A marked and significant degree of hypoglycemia was observed after approximately 80 minutes, lasting for about 300 minutes, while a maximum plasma insulin level was observed at approximately 100 minutes after the intraduodenal administration of the formulation (See FIGS. 25 and 26).

TEST 12B

TABLE 5
BLOOD SUGAR LEVELS AFTER ORAL INGESTION OF ORAL INSULIN FORMULATION

| Name | Sex | Age | Wt (Kg) | Height (cm) | ORAL INSULIN DOSE (IU/Kg) | CLASS OF DIABETES | Blood Sugar (mg/ml) at Study Time (in Hrs) 0 | 1 | 2 | 3 | 4 | 5 |
|---|---|---|---|---|---|---|---|---|---|---|---|---|
| LEE YS | M | | 55 | 161 | 0.73 | IDDM | 173.5 | 163.5 | 144.0 | 136.0 | 127.0 | 103.5 |
| LEE KW | M | | 72 | 165 | 0.64 | IDDM | *183.0 | 137.0 | 85.0 | 96.0 | 76.5 | — |
| KIM CS | F | | 46 | 150 | 0.66 | IDDM | 216.0 | 178.5 | 177.5 | 162.0 | 149.5 | — |
| LEE JS | M | | 62 | 173 | 0.65 | NIDDM | 156.0 | 152.5 | 126.0 | 118.0 | 89.5 | 86.5 |
| HONG CJ | F | | 52 | 160 | 0.65 | NIDDM | *257.5 | 259.5 | 196.5 | 183.0 | 165.0 | 136.5 |

TABLE 6
BLOOD SUGAR LEVELS AFTER ORAL INGESTION OF ORAL INSULIN FORMULATION

| Name | Sex | Age | Wt (Kg) | Height (cm) | ORAL INSULIN DOSE (IU/Kg) | CLASS OF DIABETES | Blood Sugar (mg/ml) at Study Time (in Hrs) 0 | 1 | 2 | 3 | 4 | 5 |
|---|---|---|---|---|---|---|---|---|---|---|---|---|
| LEE YS | M | | 64 | 165 | 0.63 | IDDM | *316.0 | 353.5 | 325.0 | 270.0 | 165.0 | 148.0 |
| LEE JW | M | | 82 | 169 | 0.49 | IDDM | 153.0 | 137.5 | 131.0 | 129.0 | 130.5 | — |
| MOON YJ | M | | 65 | 168 | 0.63 | IDDM | 329.0 | 247.0 | 158.0 | — | — | — |
| SHIN GS | M | | 66 | 169 | 0.49 | IDDM | 333.5 | 378.5 | 265.6 | 238.0 | 170.5 | — |
| KIM CS | F | | 67 | 159 | 0.63 | NIDDM | 157.0 | 152.0 | 137.0 | 134.0 | 130.5 | — |
| CHOI DS | M | | 59 | 165 | 0.63 | NIDDM | 209.5 | 162.5 | 97.5 | 88.0 | 86.0 | — |

*Fed Breakfast

Figure 27:
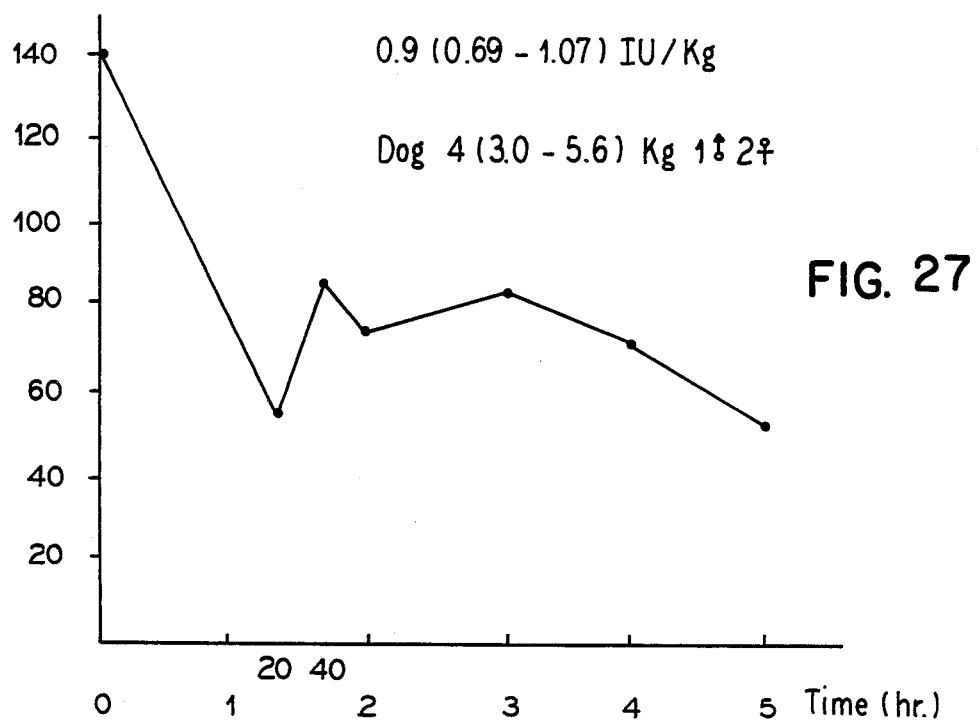
FIG. 27 illustrates the effect of the oral insulin of Example 12 on the plasma glucose levels of dogs.

The formulation of Example 11 modified as set forth in Example 12, approximately 1.0 IU per Kg, was intra-duodenally administered to a 6.0 Kg female dog. Hypoglycemic action of the formulation was compared to that of intra-duodenally administered regular injectable insulin (novo actrapid insulin, 1.0 IU per Kg) and of intravenously administered regular injectable insulin (novo actrapid insulin, 0.5 IU per Kg). After infusion of 1.26 IU of regular injectable insulin, intravenously, the plasma glucose level dropped from 102 to 23 mg/ml within 20 minutes and returned to 100 mg/ml within 3 hours. Then, 6 IU of regular injectable insulin was intraduodenally given. No changes in the blood glucose levels were observed for over a three hour period. Six (6) IU of the formulation were given, intraduodenally, and a marked and sustained reduction in blood sugar level was observed. The animal expired at two hours after the administration of the formulation due to severe hypoglycemia (see FIG. 27).

TEST 12C

After a 24 hour observation period, without insulin or oral hypoglycemic agents, and fasting overnight, three insulin-dependent and 2 non-insulin-dependent patients took approximately 0.64 to about 0.73 IU per Kg of the insulin formulation of Example 10 modified as set forth in Example 12. Blood sugar levels were measured hourly for five hours. In one IDDM and one NIDDM patient however, because of the lower fasting blood glucose levels observed prior to the study, a standard breakfast was fed and the study was continued, post-prandially. A clinically significant degree of "hypoglycemia" was observed in these patients (see Table 5 below).

Another 6 patients, 4 IDDM and 2 NIDDM patients, took 0.49 to 0.63 IU per Kg of the formulation of Example 11 modified as set forth in Example 12 orally. One patient, because of lower fasting blood sugar levels were observed, received a standard breakfast and the study was continued. In the remaining 5 cases, the study was conducted during a fasting condition. A significant degree of hypoglycemic effect was observed after the oral administration of the formulation (see Table 6 below).

12D CLINICAL STUDIES WITH GRANULAR FORMULATIONS IN DIABETICS TEST

Figure 28:
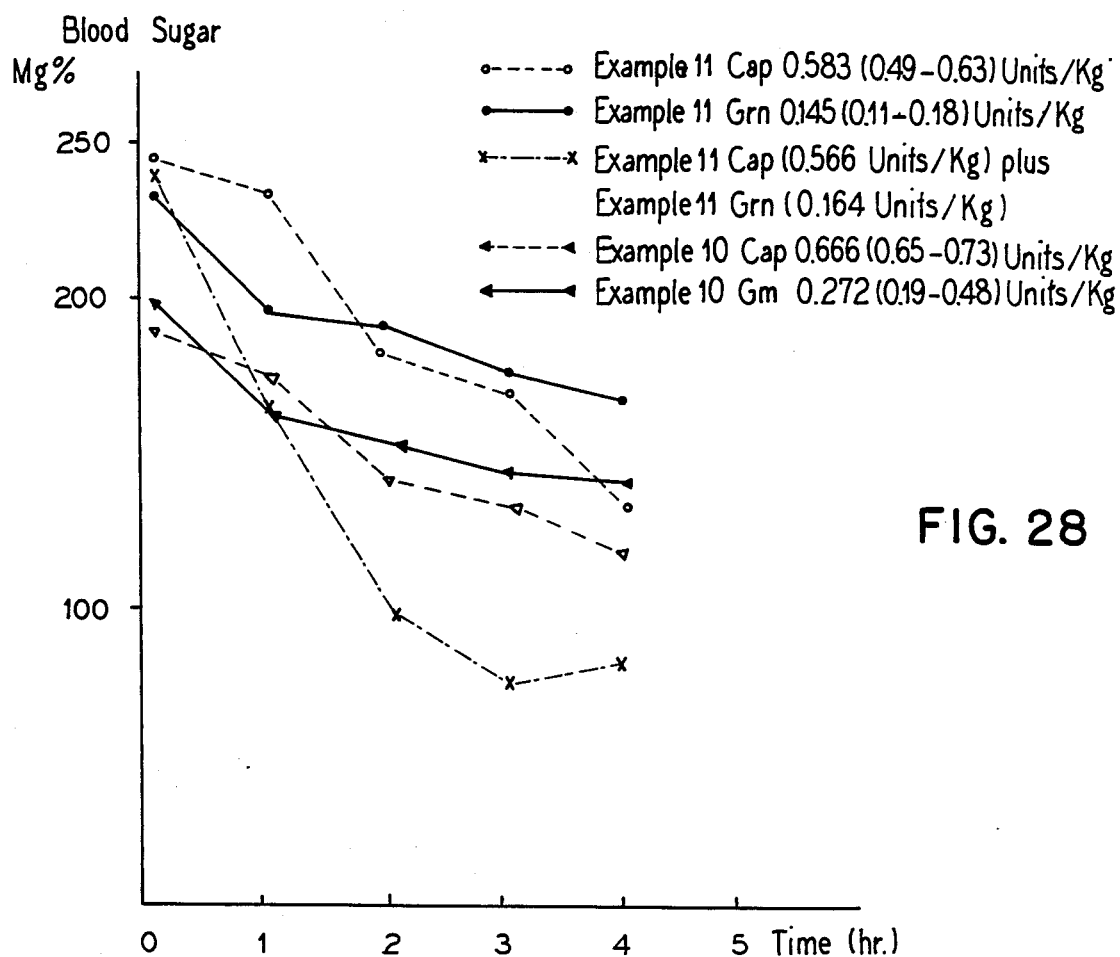
FIG. 28 illustrates the effect of the oral insulin formula of Example 11 versus the oral insulin formula of Example 12 on blood sugar.
Figure 29:
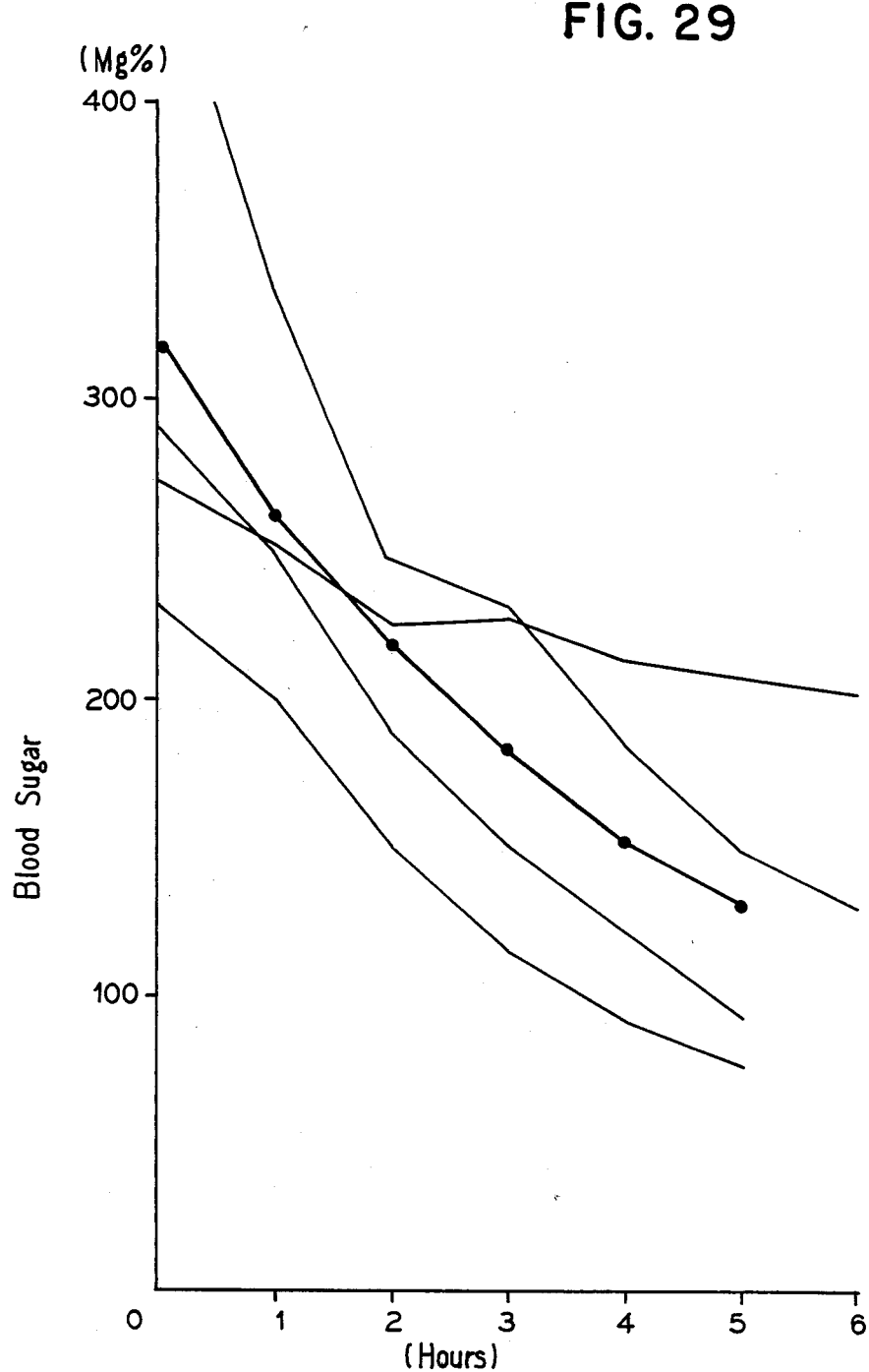
FIG. 29 illustrates the effect of the oral insulin formula of Example 13 on blood sugar.

A group of diabetics participated in studies testing the formulations of Example 10 and 11 twice over a two-week period. During the first week, each patient orally took either Example 10 or Example 11 oral insulin in #4 capsules which had been enteric coated, and one week later, the same patient took an alternative granular formulation of either Example 10 or Example 11, orally. The granular formulation of Example 11 orally administered an average insulin dose of 0.145 units per Kg of body weight (0.11 to 0.18 units per Kg body weight) and caused a faster reduction in blood sugar levels during a measured two-hour period compared to the oral administration of the Example 11 formulation in #4 capsules that had an average insulin dose of 0.583 units per Kg of body weight (0.49 to 0.63 units per Kg of weight); which is almost four (4) times the dose of the Example 11 formulation in granular form. However, the Example 11 formulation in #4 capsules lasted longer and continued to show its hypoglycemic action and effect beyond the post-two-hour dosing point (see FIG. 28). The degree of hypoglycemia induced at one-hour after the dosing of the formulation of Example 10 was slightly greater when the oral insulin formulation was given in a granular form than in #4 hard-gel capsules. However, the oral insulin formulation of Example 10 in #4 hard-gel capsules has a relatively longer lasting hypoglycemic effect than the Granular form of the oral insulin formulation of Example 10 (see FIG. 28).

Thus, ideally, a combination of the formulation of Example 10 in the granular form and in #4 hard-gel capsule form, or alternatively, a combination of the formulation of Example 11 in granular form and in #4 hard-gel capsule form may induce a rapid yet longer lasting hypoglycemic effects in diabetics. Indeed, by giving the oral insulin formulation of Example 11 in a granular form (an average 0.164 units per Kg) and in #4 hard-gel capsular formulation (an average 0.566 units per Kg) a rapid onset and longer lasting hypoglycemic effect was observed in these diabetics (see FIG. 28).

Alternatively, CF-granulated and non-granular forms of Example 10 or Example 11 (or any other Oral Insulin formulation disclosed herein) formulations of Oral Insulin may be proportionately combined and made into a hard-pressed tablet so as to obtain the combined effects of a rapid onset and long lasting hypoglycemic effect in diabetics.

EXAMPLE 13

An oral insulin formulation that had a very good hypoglycemic effect in a group of diabetics was made as follows.

Bulk (lipospherical) chemical materials, (set forth above in example 11) were added to fresh soybean powder (to inhibit tripsin, which inactivates insulin). An ovomucoid freshly prepared from egg white, according to E. Fredricq And H. F. Deutsch (J. Biol. Chem. 181: 499, 1949); was combined therewith and dissolve with crystalline insulin into a water and alcohol mix (50-50 ratio) at a pH of 7.2. Calcium chloride, 2 mm, was added to improve the physical stability of neutral insulin solutions (J. Brange and S. Havelund; Properites of insulin solution: In Artifical systems for insulin delivery, Ed. by P. BRUNETTI, et al, Raven Press, New York, pp. 83–88). The ovomucoid from egg white is a potent trypsin inhibitor. Alternatively, fresh egg white dissolved in alcohol may be used.

The following components are placed into the vessel of Spir-A-Flow.

| Components | Quantity | Maker/Lot No. (if applicable) |
|---|---|---|
| Cholesterol | 300–500 Gms | Fluka AG (CH-9470 Buchs) |
| Sodium Lauryl Sulfate | 20–40 Gm | Yakuri Kagaku, Japan (S316=05) |
| Fresh Soybean Powders | 15–30 Gm | |
| Propyl Paraben | 1–5 Gm | Junsei Chem. Co., Japan (9L1202) |
| Methyl Paraben | 5–10 Gm | Junsei Chem. Co., Japan (OC1495) |

These powderly components were ground by the Jet Mill into particles having a size of less than 50 microns. The particles were thoroughly mixed and dried in a vessel of the Spri-A-Flow under the conditions described in Example 10. The components that were dried powders were suspended in the vessel and bound with a binding solution containing insulin, ovomucoid (or egg white), and citric acid as well as a surfactant. The binding solution was prepared as follows:

| Components | Quantity | Maker/Lot No. (if applicable) |
|---|---|---|
| Triethylamine | 1.55–3.22 Gm | Wako Kagaku, Japan |
| Citric Acid | 0.08 M | Yakuri Kagaku, Japan (KA9105) |
| These chemicals were dissolved in Ethanol (100–200 ml) | | |
| Aminoacetic acid | 0.2 M | |
| Polysorbate-80 | 1–0–2.5 Gm | |
| Hydroxypropyl-cellulose-L | 5% | |

These chemicals were dissolved in approximately 100 to about 200 ml of a phosphate buffer, having pH of 8.0 the ethanol solution and phosphate buffer solution, dissolved chemicals, were mixed and insulin was added. The pH of the solution was adjusted to 7.2.

The resultant binding solution was sprayed onto the fine, dried, mid-air suspended lipospherical powders consisting of cholesterol, surfactant, soybean powder, and antimicrobial preservatives as described in Example 10.

After thoroughly drying the insulin-bound 'lipospherical powders', these powders were coated with the following coating solution:

| Chemicals | Quantity | Maker/Lot No. (if applicable) |
|---|---|---|
| Soybean Lecithin | 24 Gms | |
| Polyethyleneglycol-6000 | 15–40 Gms | Kao Sekken, Japan |
| $CaCl_2$ | 3.5–5.8 Gms | |
| Oleic Acid | 20–35 Gms | |
| Cholesterol | 1–5 Gms | |
| Methyl Paraben | 1–3 Gms | |

The above chemicals were dissolved in approximately 150 to about 400 ml of ethanol, sufficient ethanol to allow the chemicals to dissolve.

The above lipid-coating solution was sprayed onto the insulin-bound lipospherical powders as described in Example 12.

TEST 13 CLINICAL HYPOGLYCEMIC EFFECTS OF ORAL INSULIN FORMULATION

Four diabetics, 2 males and 2 females, average age 46.0 (36–56) years old, weighing an average of 60.3 (50 to 74) Kg, and having a height of 164.3 (158–168) Cm, received an average of 0.573 (0.46 to 0.68) IU per Kg of the oral insulin formulation of Example 13 after fasting. A marked and clinically significant degree of lowering in blood sugar levels was observed (see FIG. 29).

It should be understood that various changes and modifications to the preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A composition adapted for the oral administration of a selected proteinaceous material in biologically active form, said composition comprising:

(a) particles having an average diameter of approximately 1 to about 100 microns and consisting essentially of a solid emulsifying agent and a surfactant;

(b) a selected biologically active proteinaceous material bound to the surface of said particles with a binder agent; and (c) a lipid coating having a thickness of approximately 0.05 to about 1.0 microns surrounding said particles having said proteinaceous material bound to their surfaces.

2. A composition according to claim 1 further including:

(d) an enteric coating layer surrounding said lipid coating on said surfaces.

3. A composition of claim 2 wherein the proteinaceous material is insulin.

4. A composition according to claim 1 wherein the solid emulsifying agent is selected from the group consisting of cholesterol, glyceryl monostearate, oleic acid, polyethylene 50 stearate, polyoxy 40 stearate, polysorbate 20, polysorbate 40, polysorbate 60, polysorbate 80, propylene glycol diacetate, propylene glycol monostearate, arginine HCl, gum acacia, cholesterol ester, phospholipids, and fatty acids.

5. A composition according to claim 1 wherein the surfactant is selected from the group consisting of sodium lauryl sulfate, sodium stearate, stearic acid, sorbitan monolaurate, sorbitan monostearate and emulsifying wax.

6. The composition of claim 1 wherein the biologically active proteinaceous composition is selected from the group consisting of insulin, urokinase, Factor VIII, leuprolid, gangliocides, vincristine, belomyein, lidocaine, gentamicin, bretylium tosylate, cetiedile, cyclandelate, erythromycin, chloramphenicol, adriamycin, streptokinase, and cephalosporidines.

7. A composition according to claim 1 wherein the composition includes a binder agent that comprises materials selected from the group consisting of sodium carboxymethylcellulose, microcrystalline cellulose, ethylcellulose, gelatin, hydroxypropylmethylcellulose, methylcellulose, povidone, and hydroxypropylcellulose.

8. A composition according to claim 1 wherein the lipid coating comprises materials selected from the group consisting of polyethylene glycol fatty acid esters, glycerophosphatides, phosphatidylophosphates, egg yolk lecithin, oleic acid, mono, di, and tri-glycerides, stearic acid, palmitate, cholesterol, cholesterol ester, and thromethan.

9. A composition according to claim 2 wherein the enteric coating layer comprises materials selected from the group consisting of hydroxypropyl methylcellulose phthalate, polyethylene glycol-6000 shellac, cellulose phthalate, and polyvinyl acetate phthalate.

10. A composition according to claim 1 wherein said particles further include anti-microbial agents.

11. A composition according to claim 10 wherein the anti-microbial agents are selected from the group consisting of dehydroacetic acid, methylparaben, ethylparaben, phenol, phenylethyl alcohol, propylparaben, sodium benzoate, sorbic acid, thymol, thimerosal, sodium dehydroacetate, benzyl alcohol and butylparaben.

12. The composition of claim 1 including a lipolytic enzyme.

13. The composition of claim 12 wherein the lipolytic enzyme is selected from the group consisting of lipase, pancreatic lipase, amylase, protease, and bile salts.

14. A composition according to claim 1 wherein the composition further includes enzyme inhibitors.

15. A composition according to claim 14 wherein the enzyme inhibitors are selected from the group consisting of stearylamine, stearyl alcohol, triethylamine HCl, citric acid, lactic acid, pyrophosphate, triethanolamine, ethylamine tetraacetate, iodoacetamide, phenylhydrazine, hydroxylamine 3 and 8-hydroquinoline.

16. A composition according to claim 1 wherein the composition further includes antifoaming agents.

17. A composition according to claim 16 wherein the antifoaming agents are selected from the group consisting of stearyl alcohol and silicones.

18. A composition adapted for the oral administration of insulin in biologically active form, said composition comprising:
(a) particles having an average diameter of from about 1 to about 100 microns and consisting essentially of cholesterol, sodium lauryl sulfate and, methyl and propylparabens;
(b) insulin bound to the surface of said particles with a solution consisting essentially of hydroxypropylcellulose, sodium lauryl sulfate, triethylamine HCl and citric acid;
(c) a lipid coating having a thickness of from about 0.1 to 0.3 microns; and
(d) an enteric coating layer comprising hydroxypropylmethylcellulose phthalate, shellac and PEG-6000 with the thickness of 0.1 microns surrounding said polyethylene glycol monostearate coating on said particles.

19. A method for the preparation of compositions adapted for oral administration of selected proteinaceous material in biologically active form comprising the steps:
(a) forming particles having an average diameter of from about 1 micron to ½ millimeter and consisting essentially of a solid emulsifying agent and a surfactant;
(b) binding a selected biologically active proteinaceous material to the surfaces of said particles with a binder agent; and
(c) coating said particles having said proteinaceous material bound to their surfaces with a lipid coating layer having a thickness of 0.05 to 1.0 microns.

20. The method according to claim 19 further including the step of
(d) coating said particles with an enteric coating layer surrounding said lipid coating layer.

21. The method according to claim 19 further including the step of
(d) coating the particles with a water soluble coating before the lipid coating is applied.

22. The product of the process of claim 19.

23. The product of the process of claim 20.

24. The product of the process of claim 21.

25. A composition adapted for the oral administration of insulin in biologically active form comprising:
particles having an average diameter of approximately 1 to 100 microns consisting essentially of an emulsifying agent and a surfactant;
insulin bound to the surface of the particles;
a lipid coating surrounding the particles having the proteinaceous material bond to their surfaces; and
an enteric coating layer surrounding the lipid coating.

26. A method of orally administering insulin comprising:
providing a composition for oral ingestion comprising insulin bound to a surface of a solid emulsifier/solubilizing particle, the insulin and particles being coated with a lipid coating, the particles having an average diameter of approximately 1 micron to about 100 microns, and the lipid coating being coated by an enteric coating.

27. A method orally administering insuling composition:
providing a composition for oral ingestion comprising insulin bound to a surface of lipoprotein particles, the insulin and particles being coated by a lipid coating, and the lipid coating being coated by an enteric coating.

28. The method of claim 27 including the step of administering a lipolytic enzyme.

29. The method of claim 27 including orally administering at least one second capsule containing at least one lipolytic enzyme.

30. A composition adapted for the oral administration of a selected proteinaceous material in biologically active form, said composition comprising:
(a) a lipoprotein composition;

(b) a selected biologically active proteinaceous material bound to the surface of the lipoprotein composition; and (c) a lipid coating surrounding said lipoprotein composition and proteinaceous material.

31. The composition of claim 30 including a water soluble coating surrounding the lipoprotein and proteinaceous material, the lipid coating coating the water soluble coating.

32. The composition of claim 30 wherein the liproprotein is low density lipoprotein.

33. The composition of claim 30 wherein the lipoprotein comprises at least one amino acid.

34. The composition of claim 30 including a gel capsule, the lipid coating material being packed into the gel capsule.

35. The composition of claim 34 wherein the gel capsule is coated with an enteric coating.

36. The composition of claim 30 wherein the biologically active proteinaceous composition is selected from the group consisting of insulin, urokinase, Factor VIII, leuprolid, gangliocides, vincristine, belomyein, lidocaine, gentamicyin, bretylium, tosylate, cetiedile, cyclandelate, erythromycin, chloroamphenicol, adriamycin, streptokinase, and cephalosporidines.

37. The composition of claim 30 including a lipolytic enzyme.

38. The composition of claim 37 wherein the lipolytic enzyme is selected from the group consisting of lipase, pancreatic lipase, amylase, protease, and bile salts.

39. The composition of claim 38 wherein the lipolytic enzyme comprises lipase and bile salts.

40. A composition according to claim 30 wherein the lipid coating comprises materials selected from the group consisting of polyethylene glycol fatty acid esters, glycerophosphatides, phosphatidylophosphates, egg yolk lecithin, oleic acid, mono, di, and tri-glycerides, stearic acid, palmitate, cholesterol, cholesterol ester, and thromethan.

41. A composition according to claim 35 wherein the enteric coating layer comprises materials selected from the group consisting of hydroxypropyl methylcellulose phthalate, polyethylene glycol-6000 shellac, cellulose phthalate, and polyvinyl acetate phthalate.

42. A composition according to claim 30 wherein said particles further include anti-microbial agents.

43. A composition according to claim 42 wherein the anti-microbial agents are selected from the group consisting of dehydroacetic acid, methylparaben, ethylparaben, phenol, phenylethyl alcohol, propylparaben, sodium benzoate, sorbic acid, thymol, thimersal, sodium dehydroacetate, benzyl alcohol and butylparaben.

44. A composition according to claim 30 wherein the composition further includes enzyme inhibitors.

45. A composition according to claim 44 wherein the enzyme inhibitors are selected from the group consisting of stearylamine, stearyl alcohol, triethylamine HCl, citric acid, lactic acid, pyrophosphate, triethanolamine, ethylamine tetraacetate, iodoacetamide, phenylhydrazine, hydroxylamine 3 and 8-hydroquinoline.

46. A composition according to claim 30 wherein the composition further includes antifoaming agents.

47. The composition according to claim 30 wherein the lipoprotein includes a lipid and an amino acid.

48. The composition of claim 47 where in the lipid is selected from the group consisting of cholesterol, oleic acid, stearic acid, sodium lauryl sulfate, lecithin, phosphatides, sodium lauryl sulfate and lecithin, palmitic and phosphatide phosphate choline.

49. The composition of claim 47 wherein the amino acid is selected from the group consisting of arginine, lysine, histidine, and aspartic acid.

50. A composition according to claim 46 wherein the antifoaming agents are selected from the group consisting of stearyl alcohol and silicones.

51. A composition adapted for the oral administration of insulin in biologically active form, said composition comprising:

(a) particles having an average diameter of from about 1 micron to about ½ millimeter and including a low density of lipoprotein composition;

(b) insulin bound to the surface of said particles with a binder;

(c) a water soluble coating layer, for coating the particles and insulin; and (d) a lipid coating for coating the water soluble layer, particles and insulin.

52. The composition of claim 51 including a lipolytic enzyme.

53. The composition of claim 51 including an enteric coating layer for coating the lipid layer.

54. A method for the preparation of compositions adapted for the oral administration of selected proteinaceous material in biologically active form comprising the steps of:

(a) forming low density lipoprotein particles having an average diameter of from about 1 micron to ½ millimeter;

(b) binding a selected biologically active proteinaceous material to the surfaces of said particles with a binder agent;

(c) coating the particles and proteinaceous material with a water soluble coating; and (d) coating the water soluble coated particles having said proteinaceous material bound to their surfaces with a lipid coating layer having a thickness of 0.05 to 1.0 microns.

55. A method according to claim 54 further including the step (e) coating said particles with an enteric coating layer surrounding said lipid coating layer.

56. The product of the process of claim 54.

57. The product of the process of claim 55.

58. A composition adapted for the oral administration of insulin in biologically active form comprising:

low density lipoprotein particles;

insulin bound to the surface of the particles;

a water soluble coating surrounding the particles and insulin;

a lipid coating surrounding the water soluble coating and particles having insulin bound to their surfaces;

a gel capsule for surrounding the lipid coating; and an enteric coating layer surrounding the gel capsule.

59. A method of treating diabetes comprising the steps of:

administering orally at least one capsule having a composition including a low density lipoprotein, insulin bound to the lipoprotein, a water soluble coating over the insulin and lipoprotein, and a lipid coating over the water soluble coating; and administering orally at least one capsule having a composition icluding lipolytic enzymes and bile salts.

60. The method of treating diabetes comprising the steps of:

administering orally at least one capsule having a composition including emulsifier/solubilizer particles, insulin bound to the particles, and a lipid coating over the particles; and administering orally at least one capsule having a composition including lipolytic enzymes.

61. A composition useful for the oral administration of a proteinaceous compound comprising lipolytic enzymes selected from the group including, pancreatic lipase, amylase, protease, and bile salts.

62. The composition of claim 61 wherein the lipolytic enzymes selected are pancreatic lipase and bile salts.

63. A composition adapted for the oral administration of insulin comprising the following components:
  (a) particles of pancreatic lipase;
  (b) particles of bile salt;
  (c) lipid coated insulin bound lipid particles;
  (d) sodium bicarbonate; and
  (e) citric acid.

64. The composition of claim 63 wherein the components are placed in hard gel capsules.

65. The composition of claim 63 wherein the components are pressed into tablets.

66. The composition of claim 63 wherein the weight percent ratio of sodium bicarbonate to citric acid is between 3:1 to 1:1.

67. The composition of claim 63 wherein the insulin bound particle has a spherical size of less than 1.5 millimeters.

68. The composition of claim 63 wherein the pancreatic lipase and bile salt particles are enteric coated.

69. A composition adapted for the oral administration of insulin comprising a sodium bicarbonate and citric acid mixture in a ratio of approximately 3:1 to about 1:1, the mixture forming a seed that is coated with a layer of an insulin lipid mixture, and a resultant particle is then coated with an enteric coating.

* * * * *